US008116886B2

(12) United States Patent
Simaan et al.

(10) Patent No.: US 8,116,886 B2
(45) Date of Patent: Feb. 14, 2012

(54) ELECTRODE ARRAYS AND SYSTEMS FOR INSERTING SAME

(75) Inventors: Nabil Simaan, New York, NY (US); Spiros Manolidis, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 443 days.

(21) Appl. No.: 11/581,899

(22) Filed: Oct. 16, 2006

(65) Prior Publication Data

US 2007/0225787 A1     Sep. 27, 2007

Related U.S. Application Data

(60) Provisional application No. 60/726,770, filed on Oct. 14, 2005, provisional application No. 60/772,796, filed on Feb. 13, 2006, provisional application No. 60/781,994, filed on Mar. 13, 2006.

(51) Int. Cl.
*A61N 1/08* (2006.01)
(52) U.S. Cl. .................................. 607/137
(58) Field of Classification Search ............ 606/108, 606/129, 109; 128/899; 607/55–57, 137; 623/10, 24–25
See application file for complete search history.

(56) References Cited

U.S. PATENT DOCUMENTS

| 2,286,571 | A | 6/1942 | Pollard |
| 4,393,728 | A | 7/1983 | Larson et al. |
| 4,551,061 | A | 11/1985 | Olenick |
| 4,940,050 | A * | 7/1990 | Forssmann et al. ............... 601/4 |
| 4,956,790 | A | 9/1990 | Tsuchihashi et al. |
| 5,906,591 | A | 5/1999 | Dario et al. |
| 6,272,371 | B1 * | 8/2001 | Shlomo ......................... 600/424 |
| 6,390,970 | B1 * | 5/2002 | Muller ............................ 600/25 |
| 6,493,573 | B1 * | 12/2002 | Martinelli et al. ............ 600/424 |
| 6,748,255 | B2 * | 6/2004 | Fuimaono et al. ............ 600/374 |

(Continued)

FOREIGN PATENT DOCUMENTS

WO    WO-01/10292    2/2001

OTHER PUBLICATIONS

6th European Congress of Oto-Rhino-Laryngology, Eur Arch Otorhinolaryngol (2007) (Suppl 1) 264:S153-S264.

(Continued)

*Primary Examiner* — Niketa Patel
*Assistant Examiner* — Hiba El-Kaissi
(74) *Attorney, Agent, or Firm* — Wilmer Cutler Pickering Hale and Dorr LLP

(57) ABSTRACT

Electrode arrays and systems for inserting same are disclosed. In some embodiments, electrode arrays are provided, the electrode arrays comprising: a passive-bending portion; an active-bending portion coupled to the passive bending portion; a plurality of electrodes located in at least one of the passive-bending portion and the active bending portion; and an actuator that causes the active-bending portion to deflect from the passive-bending portion. In some embodiments, systems for inserting an electrode array in the body are provided, the systems comprising: an insertion module for controllably inserting the electrode array in the body and sensing forces applied to the electrode array; a monitor for providing information to a user; and a controller coupled to the insertion module and the monitor, wherein the controller causes the insertion module to control an amount of force that is applied to the electrode array.

23 Claims, 16 Drawing Sheets

U.S. PATENT DOCUMENTS

| | | | | |
|---|---|---|---|---|
| 6,970,730 | B2* | 11/2005 | Fuimaono et al. | 600/374 |
| 6,973,340 | B2* | 12/2005 | Fuimaono et al. | 600/374 |
| 7,257,434 | B2* | 8/2007 | Fuimaono et al. | 600/374 |
| 2002/0173799 | A1* | 11/2002 | Besharim et al. | 606/108 |
| 2003/0114846 | A1* | 6/2003 | Fuimaono et al. | 606/41 |
| 2005/0085715 | A1* | 4/2005 | Dukesherer et al. | 600/424 |
| 2005/0085720 | A1* | 4/2005 | Jascob et al. | 600/424 |
| 2006/0167472 | A1* | 7/2006 | Hong et al. | 606/129 |
| 2008/0147173 | A1* | 6/2008 | Mciff et al. | 623/1.34 |

OTHER PUBLICATIONS

Adunka, O. et al., "Development and Evaluation of an Improved Cochlear Implant Electrode Design for Electric Acoustic Stimulation," Laryngoscope 114: Jul. 2004, pp. 1237-1241.

Adunka, O. et al., "Preservation of Basal Inner Ear Structures in Cochlear Implantation," ORL J. Otorhinolaryngol Relat Spec, vol. 66, pp. 306-312, 2004.

Anon, "Going where others have not gone before," The Industrial Robot, Mar. 1985, pp. 36-37.

Ascari, L., "A New Active Microendoscope for Exploring the Subarachnoid Space in the Spinal Cord," International Conference on Robotics and Automation, pp. 2657-2662, 2003.

Avriel, M., "Nonlinear Programming Analysis and Methods," Prentice-Hall, Inc., 1976.

Ballay, C. et al., "Steady-State Response Audiometry in a Group of Patients with Steeply Sloping Sensorineural Hearing Loss," Laryngoscope, 115: 1243-1246, 2005.

Battmer, R.D. et al., "Evaluation of the Neural Response Telemetry (NRT) capabilities of the Nucleus Research Platform 8: initial results from the NRT trial," International Journal of Audiology 2004; 43: S10-S15.

Bhatti, P.T. et al., "A High-Density Electrode Array for Cochlear Prosthesis," NSF Engineering Research Center for Wireless Integrated MicroSystems, pp. 1750-1753, NSF Engineering Research Center for Wireless Integrated MicroSystems, University of Michigan and Michigan Technological University, pp. 1750-1753.

Brown, C.W. et al., "A Novel GJB2 (Connexin 26) Mutation, F14L, in a Patient with Unusual Mucocutaneous Findings and Deafness," The Journal of Investigative Dermatology, Letters to the Editor, vol. 121, No. 5, Nov. 2003, pp. 1221-1223.

Canny, J., "The Complexity of Robot Motion Planning," 1998.

CDC, Center for Disease Control and Prevention, "Hearing loss statistics," http://www.cdc.gov/ncbddd/dd/ddhi.htm.

Chen, B.K. et al., "Evaluation of trajectories and contact pressures for the straight nucleus cochlear implant electrode array—a two dimensional application of finite element analysis," Medical Engineering & Physics 25 (2003) 141-147.

Chen, G. et al., "Identification of the Flexible Actuator of a Colonoscope," Proceedings of the 2003 IEEE/RSJ Intl. Conference on Intelligent Robots and Systems, Las Vegas Nevada, Oct. 2003, pp. 3355-3360.

Chen, W. et al., "Linkage of otosclerosis to a third locus (OTSC3) on human chromosome 6p21.3-22.3," J. Med. Genet. 2002, 39; 473-477.

Chirikjian, G.S. et al., "A Hyper-Redundant Manipulator," IEEE Robotics and Automation Magazine, pp. 22-29, 1994.

Chirikjian, G.S. et al., "A Modal Approach to Hyper-Redundant Manipulator Kinematics," IEEE Transactions on Robotics an Automation, vol. 10, No. 3, Jun. 1994, pp. 343-354.

Chirikjian, G.S. et al., "An Obstacle Avoidance Algorithm for Hyper-Redundant Manipulators," IEEE International Conference on Robotics and Automation, pp. 625-631, 1990.

Chirikjian, G.S. et al., "Design and Experiments with a 30 DOF Robot," IEEE International Conference on Robotics on Robotics and Automation, pp. 113-119, 1993.

Chirikjian, G.S. et al., "Kinematically Optimal Hyper-Redundant Manipulator Configurations," IEEE Transactions on Robotics and Automation, vol. 11, pp. 794-806, 1995.

Chirikjian, G.S., "General Methods for Computing Hyper-Redundant Manipulator Inverse Kinematics," IEEE/RSJ International conference on Intelligent Robots and Systems (IROS), pp. 1067-1073, 1993.

Chirikjian, G.S.I. et al., "A Geometric Approach to Hyper-Redundant Manipulator Obstacle Avoidance," ASME Jouran of Mechanical Design, vol. 114, pp. 580-585, 1992.

Cohen, L.T., "Improved and Simplified Methods for Specifying Positions of the Electrode Bands of a Cochlear Implant Array," The American Journal of Otology, vol. 17, No. 6, 1996, pp. 859-865.

Cohen, N.L. et al., "Surgical Technique for the Nucleus Contour Cochlear Implant," Ear & Hearing, Feb. 2002. pp. 59S-66S.

Cox, D. et al., "Ideals, Varieties, and Algorithms," Springer, 1996.

Creighton, F.M. et al., "Safe Superconducting Current Discharge for the Magnetic Stereotaxis System," IEEE Transactions on Magnetics, vol. 35, No. 5, Sep. 1999, pp. 4285-4290.

D'Attanasio, S. et al., "A Semi-Automatic Handheld Mechatronic Endoscope with Collision-Avoidance Capabilities," Proceeding of the 2000 IEEE International Conference on Robotics & Automation, San Francisco, CA, Apr. 2000.

Dandurand, A., "The Rigidity of Compound Spatial Grids," Structural Topology #10, 1984, pp. 40-56.

Dario, P. et al., "A Miniature Steerable End-Effector for Application in an Intergrated System for Computer-Assisted Arthroscopy," IEEE International Conference on Robotics and Automation, pp. 1573-1579, 1997.

Dario, P. et al., "Development and in Vitro Testing of a Miniature Robotic System for Computer-Assisted Colonoscopy," Computer Aided Surgery 4:1-14 (1999).

Dasgupta, B. et al., "The Stewart platform manipulator: a review," Mechanism and Machine Theory 35 (2000) 15-40.

Della Santa, A. et al., "Steerable Microcatheters Actuated by Embedded Conducting Polymer Structures," Journal of Intelligent Material Systems and Structures, vol. 7—May 1996, p. 292-300.

Dhingra, A.K. et al., "A Grobner-Sylvester Hybrid Method for Closed-Form Displacement Analysis of Mechanisms," Journal of Mechanical Design, Dec. 2000, vol. 122, pp. 431-438.

Dietmaier, P. "The Stewart-Gough Platform of General Geometry Can Have 40 Real Postures," Advances in Robot Kinematics: Analysis and Control, 1986, pp. 7-16.

Ebert-Uphoff, I. et al., "Inverse Kinematics of Discretely Actuated Hyper-Redundant Manipulators Using Workspace Densities," Proceeding of the 1993 International Conference on Robotics and Automation, Minneapolis, Minnesota—Apr. 1996, pp. 139-145.

Eshraghi, M.D., A.A. et al., "Comparative Study of Cochlear Damage With Three Perimodiolar Electrode Designs," Laryngoscope 113, Mar. 2003, pp. 415-419.

Faugere, J.C. et al., "Combinatorial Classes of Parallel Manipulators," Mech. Mach. Theory vol. 30, No. 6, pp. 756-776, 1995.

Fichter, E.F., "A Stewart Platform-Based Manipulator: General Theory and Practical Construction," The International Journal of Robotics Research, vol. 5, No. 2, Summer 1986, pp. 157-182.

Fishman, A.J. et al., "Fluoroscopically Assisted Cochlear Implantation," Otology & Neurotology, vol. 24, No. 6, 2003, pp. 882-886.

Gantz, M.D., B.J. et al., "Preservation of Hearing in Cochlear Implant Surgery: Advantages of Combined Electrical and Acoustical Speech Processing," Laryngoscope, 115: 796-802, May 2005.

Ghanzvini, M., "Reducing the Inverse Kinematics of Manipulators to the Solution of a Generalized Eigenproblem," Computational Kinematice, J. Angeles et al. (eds.), 1993, pp. 15-26.

Gosselin, C. et al., "Singularity Analysis of Closed-Loop Kinematic Chains," IEEE Transactions on Robotics and Automation, vol. 6, No. 3, Jun. 1990, pp. 281-290.

Gough, V.E. et al., "Universal Tyre Test Machine," Proceedings, Ninth International Technical Congress F.I.S.T.A., 1962, pp. 117-137.

Grace, K.W., "Kinematic Design of an Opthalmic Surgery Robot and Feature Extracting Bilateral Manipulation," in Mechanical Engineering: Northwestern University, 1995.

Gravagne, I.A. et al., "Kinematic Transformations for Remotely-Actuated Planar Continuum Robots," Proceedings of the 2000 IEEE International Conference on Robotics & Automation, San Francisco, CA, Apr. 2000, pp. 19-26.

Gravagne, I.A. et al., "On the Kinematics of Remotely-Actuated Continuum Robots," Proceedings of the 2000 IEEE International Conference on Robotics & Automation, San Francisco, CA, Apr. 2000, pp. 2544-2550.

Gstoettner, W. et al., "Hearing Preservation in Cochlear Implantation for Electric Acoustic Stimulation," Acta Otolaryngol 2004; 124: 348-352.

Guo, S. et al., "Micro Active Guide Wire Catheter System—Characteristic Evaluation, Electric Model and Operablity Evaluation of Micro Active Catheter-," Proceeding of the 1996 IEEE International Conference on Robotics and Automation, Minneapolis, Minnesota—Apr. 1996, pp. 2226-2231.

Guo, S. et al., "Micro Active Guide Wire Catheter System—Characteristic Evaluation, Electrical Model and Operability Evaluation of Micro Active Catheter-," Sixth International Symposium on Micro Machine and Human Science, IEEE 1995, pp. 131-136.

Guo, S. et al., "Micro Active Guide Wire Catheter System," IEEE 1995, pp. 172-177.

Guo, S. et al., "Micro Catheter System with Active Guide Wire," IEEE International Conference on Robotics and Automation, 1995, pp. 79-84.

Haga, Y. et al., "Small Diameter Active Catheter Using Shape Memory Alloy," IEEE 1998, pp. 419-424.

Hale, J.R. et al., "Medical Applications of Magnet Devices," IEEE Transactions on Magnetics, vol. Mag-11, No. 5, Sep. 1975.

Hannan, M.W. et al., "Analysis and Initial Experiments for a Novel Elephant's Trunk Robot," Proceedings of the 2000 IEEE/RSJ International Conference on Intelligent Robots and Systems, IEEE 2000, pp. 330-337.

Hannan, M.W. et al., "The 'Elephant Trunk' Manipulator, Design and Implementation," 2001 IEEE/ASME International Conference on Advanced Intelligent Mechatronics Proceedings, Jul. 8-12, 2001—Como, Italy, pp. 14-19.

Hirai, S. et al., "Modeling of Deformable Thin Parts for Their Manipulation," IEEE 1994, pp. 2955-2960.

Hirai, S. et al., "Towards a Task Planning for Deformable Object Manipulation—Formulation and Computation of Linear Object Deformation," IEEE 1995, pp. 80-85.

Hirose, S. "Biologically Inspired Robots, Snake-Like Locomotors and Manipulators," Oxford University Press, 1993.

Hirose, S. et al., "Coupled Tendon-driven Multijoint Manipulator," Proceedings of the 1991 IEEE, International Conference on Robotics and Automation, Sacramento, California—Apr. 1991, pp. 1268-1275.

Hirose, S. et al., "The Development of Soft Gripper for the Versatile Robot Hand," Mechanism and Machine Theory, 1978, vol. 13, pp. 351-359.

Hodges, A.V. et al., "Conservation of Residual Hearing with Cochlear Implantation," The American Journal of Otology, 1997, 18:179-183.

Hunt, K.H. "Structural Kinematics of In-Parallel-Actuated Robot-Arms," Journal of Mechanisms, Transmissionsm and Automation in Design, Dec. 1983, vol. 105, pp. 705-712.

Husty, M.L. "An Algorithm for Solving the Direct Kinematics of General Stewart-Gough Platforms," Mech. Mach. Theory vol. 31, No. 4, pp. 365-380, 1996.

Huttenbrink, K.-B. et al., "Movements of Cochlear Implant Electrodes Inside the Cochlea during Insertion: An X-ray Microscopy Study," Otology & Neurotology, 23: 198-191, 2002.

Ikuta, K., K. Yamamoto, and K. Sasaki. Development of Remote Microsurgery Robot and New Surgical Procedure for Deep and Narrow Space. in IEEE International Conference on Robotics and Automation. 2003.

Immega, G. et al., "The KSI Tentacle Manipulator," IEEE International Conference on Robotics and Automation, IEEE 1995, pp. 3149-3154.

Innocenti, C., "Forward Kinematics in Polynomial Form of the General Stewart Platform," Transactions of the ASME, vol. 123, Jun. 2001, pp. 254-260.

Ishiyama, K. et al., "Magnetic micromachines for medical applications," Journal of Magnetism and Magnetic Materials, 242-245 (2002) 41-46.

James, C. et al., "Preservation of residual hearing with cochlear implantation: How and why," Acta Oto-Laryngologica, 2005; 125: 481-491.

Kapoor, A. et al., "A System for Speed and Torque Control of DC Motors with Application to Small Snake Robots," Accepted for presentation at IEEE Mechantronics & Robotics, Aachen, Germany, Sep. 13-15, 2004., pp. 1-6.

Kapoor, A. et al., "Suturing in Confined Spaces: Constrained Motion Control of a Hybrid 8-DoF Robot," Submitted to IEEE International Conference on Advanced Robotics, Seattle, Washington, USA (ICAR Jul. 18, 2005), pp. 1-8.

Karger, A. "Architecture Singular Parallel Manipulators," Advances in Robot Kinematics: Analysus and Control, 1998, pp. 445-454.

Ketten, Ph.D., D.R. et al., "In Vivo Measures of Cochlear Length and Insertion Depth of Nucleus Cochlear Implant Electrode Arrays," Ann Otol Rhinol Laryngol 107: 1998, pp. 1-18.

Kha, H.N. et al., "Stiffness properties for Nucleus standard straight and contour electrode arrays," Medical Engineering & Physics 26 (2004) 677-685.

Kiefer, J. et al., "Conservation of Low-frequency Hearing in Cochlear Implantation," Acta Otolaryngol 2004; 124; 272-280.

Kutz, M.D., W. et al., "Neuropsychological Testing in the Screening for Cochlear Implant Candidacy," Laryngoscope 113: Apr. 2003, pp. 763-766.

Lazard, D. "On the Representation of Rigid-Body Motions and its Application to Generalized Platform Manipulators," Computational Kinematics, 1993, pp. 175-181.

Li, C. et al., "Design of Continuous Backbone, Cable-Driven Robots," Journal of Mechanical Design, Jun. 2002, vol. 24, pp. 265-271.

Li, Y. et al., "Design and study of a novel hyper-redundant manipulator," Robotica (2003), vol. 21, pp. 505-509.

Lim, G. et al., "Multi-link active catheter snake-like motion," Robotica (1996) vol. 14, pp. 499-506.

Lim. G. et al., "Future of active catheters," Sensors and Actuators A 56 (1996) 113-121.

Lisboa, O. et al., "An optical-fiber bending sensor using two-mode fibers with an off-center core," Smart Mater. Struct. 3 (1994) 164-170.

Liu, Z. et al., "Learning Insertion Task of a Flexible Beam by Virtual Agents," Proceedings of the 2002 IEEE International Conference on Robotics & Automation, Washington, DC, May 2002, pp. 3290-3295.

Liu, Z. et al., "Learning the insertion operation of a flexible beam into a hole with a manipulator," Artif Life Robotics (2002) 6:155-162.

Ma, O. et al., "Architecture Singularities of Platform Manipulators," Proceedings of the 1991 IEEE International Conference on Robotics and Automation, Sacramento, California—Apr. 1991, pp. 1542-1547.

Manolidis, S. et al., "Do the Genes That Cause Otosclerosis Reduce Susceptibility to Otitis Media," Otology & Neurotology, 24: 868-871.

Manolidis, S. et al., "Use of Reconstructed, Non-Orthogonal Plane, High-Resolution Computed Tomography of the Temporal Bone in the Planning of Temporal Bone Surgery," ORL, 2003; 65: 71-75.

Meeker, D.C. et al., "Optimal Realization of Arbitrary Forces in a Magentic Stereotaxis System," IEEE Transactions on Magnetics, vol. 32, No. 2, Mar. 1996., pp. 320-328.

Merlet, J-P., "Kinematics' not dead!" Proceedings of the 2000 IEEE International Conference on Robotics & Automation, San Francisco, CA—Apr. 200, pp. 1-6.

Merlet, J-P., "Parallel Robots: Open Problems," Robotics Research the Ninth International Symposium, 1999, pp. 27-32.

Merlet, J-P., "Singular Configurations of Parallel Manipulators and Grassmann Geometry," The International Journal of Robotics Research, vol. 8, No. 5, Oct. 1989, pp. 45-56.

Merlet, J., "Parallel Robots," Kluwer Academic Publishers, 2000.

Merlet, J.-P., "Parallel manipulators: state of the art and perspectives," Advanced Robotics, vol. 8, No. 6, pp. 589-596 (1994).

Miller, J.M. et al., "Cochlear Implants: models of the Electrically Stimulated Ear," pp. 44- 47, 1990.

Mineta, T. et al., "Batch fabricated flat meandering shape memory alloy actuator for active catheter," Sensors and Actuators A 88 (2001) pp. 112-120.

Mochiyama, H. et al., "Direct Kinematics of Manipulators with Hyper Degrees of Freedom and Frenet-Serret Formula," Proceedings of the 1998 IEEE, International Conference on Robotics & Automation, Leaven, Belgium—May 1998, pp. 1653-1658.

Mochiyama, H. et al., "Shape Correspondence between a Spatial Curve and a Manipulator with Hyper Degrees of Freedom," Proceedings of the 1988 IEEE/RSJ, Ind. Conference on Intelligent Robots and Systems, Victoria, B.C., Canada—Oct. 1998, pp. 161-166.

Mochiyama, H. et al., "The Shape Jacobian of a Manipulator with Hyper Degrees of Freedom," Proceedings of the 1999 IEEE, International Conference on Robotics & Automation, Detroit, Michigan, May 1999, pp. 2837-2842.

Moll, M. et al., "Path Planning for Variable Resolution Minimal-Energy Curves of Constant Length," Proceedings of the 2005 IEEE, International Conference on Robotics and Automation, Barcelona, Spain, Apr. 2005, pp. 2130-2135.

Moller, H.M., "Grobner Bases and Numerical Analysis," Grobner Bases and Applications, London Mathematical Society Lecture Note Series 251, 1998, pp. 159-178.

Montesi, M.C. et al., "An SMA-based flexible active endoscope for minimal invasive surgery," J. Micromech. Microeng. 5 (1995) 180-182.

Nakagaki, H. et al., "Study of Insertion Task of a Flexible Beam into a Hole," IEEE International Conference on Robotics and Automation, IEEE 1995, pp. 330-335.

Nakagaki, H. et al., "Study of Insertion Task of a Flexible Wire into a Hole by Using Visual Tracking Observed by Stereo Vision," Proceedings of the 1996 IEEE International Conference on Robotics and Automation, Minneapolis, Minnesota—Apr. 1996, pp. 3209-3214.

NIDCD, "Presbycusis according to NIDCD," www.nidcd.nih.gov/health/hearing/presbycusis.asp, NIH Pub. No. 97-4235, Oct. 1997, Contact information updated 2002.

Nielsen, J. et al., "Solving the Input/Output Problem for Planar Mechanisms," Transactions of the ASME, vol. 121, Jun. 1999, pp. 206-211.

Oghalai, M.D., J.S. et al., "Neonatal Hearing Loss in the Indigent," Laryngoscope 112: Feb. 2002, pp. 281-286.

Osuka, K. et al., "Development of Mobile Inspection Robot for Rescue Activities: MOIRA," Proceedings of the 2003 IEEE/RSJ Intl. Conference on Intelligent Robots and Systems, Las Vegas, Nevada—Oct. 2003, pp. 3373-3377.

Paljug, E. et al., "The JPL Serpentine Robot: 1 12 DOF System for Inspection," IEEE International Conference on Robotics and Automation, 1995 IEEE, pp. 3143-3148.

Park, K. et al., "A Multilink Active Catheter with Polyimide-Based Integrated CMOS Interface Circuits," Journal of Microelectromechanical Systems, vol. 8, No. 4, Dec. 1999, pp. 349-357.

Park, K. et al., "An integrated communication and control system for a multi-link active catheter," J. Micromech. Microeng. 6 (1996) 345-351.

Patrick, MSc., J.F., et al., "Characterization of Mechanical Properties of Single Electrodes and Multielectrodes," Annals of Otology, Rhinology and Laryngologyment, vol. 96, pp. 46-48, 1987.

Peirs, J. et al., "Design of an advanced tool guiding systems for robotid surgery," Proceedings of the 2003 IEEE, International Conference on Robotics & Automation, Taipei, Taiwan, Sep. 14-19, 2003, pp. 2651-2656.

Phee, L. et al., "Analysis and Development of Locomotion Devices for the Gastroinstestinal Tract," IEEE Transactions on Biomedical Engineering, vol. 49, No. 6, Jun. 2002, pp. 613-616.

Raghavan, M. et al., "Solving Polynomial Systems for the Kinematic Analysis and Synthesis of Mechanisms and Robot Manipulators," Special 59th Anniversary Design Issue, Jun. 1995, vol. 117, pp. 71-79.

Raghavan, M., "The Stewart Platform of General Geometry Has 40 Configurations," Journal of Mechanism Design, Jun. 1993, vol. 115, pp. 277-282.

Reynaerts, D. et al., "Shape memory micro-actuation for a gastrointestinal intervention system," Sensors and Actuators 77 (1999) 157-166.

Rhode, F.V. "Large Deflections of a Cantilever Beam with Uniformly Distributed Load," Q. Appl. Math., vol. 11, pp. 337-338, 1953.

Robinson, G. et al., "Continuum Robots—A State of the Art," Proceedings of the 1999 IEEE International Conference on Robotics & Automation, Detroit, Michigan—May 1999, pp. 2849-2854.

Roland, Jr., J.T. "A Model for Cochlear Implant Electrode Insertion and Force Evaluation: Results with a New Electrode Design and Insertion Technique," Laryngoscope, 115: 1325-1339, 2005.

Roth, B. "Computations in Kinematics," Computational Kinematics, 1993, pp. 3-14.

Schreiber, R.R. "Volvo Chooses Spine Robot for Spray Operations," Robotics Today, 1984, pp. 28.

Shahinpoor, M. et al., "Ionic Polymer-Metal Composites (IPMC) As Biomimetic Sensors and Actuators," Proceedings of SPIE's 5th Annual International Symposium on Smart Structures and Materials, Mar. 1-5, 1998, pp. 1-17.

Simaan, N, et al., "Remarks on 'Hidden' Lines in Parallel Robots," 7th International Symposium on Advances in Robot Kinematics (ARK 2000), Piran-Portoroz, Slovenia, 2000.

Simaan, N. "Analysis and Synthesis of Parallel Robots for Medical Applications," in Mechanical Engineering, vol. M.Sc. Haifa, Israel, 1998.

Simaan, N. "Snake-Like Units Using Flexible Backbones and Actuation Redundancy for Enhanced Miniaturization," Proceedings of the 2005 IEEE, International Conference on Robotivs and Automation, Barcelona, Spain, Apr. 2005, pp. 3012-3017.

Simaan, N. et al., "A Dexterous System for Laryngeal Surgery," Proceedings of the 2004 IEEE, International Conference on Robotics & Automation, New Orleans, LA—Apr. 2004, pp. 351-357.

Simaan, N. et al., "A System for Macro-Micro Distal Dexterity Enhancement in Micro Surgery of the Eye," USA: Johns Hopkins University, 2004. (abstract).

Simaan, N. et al., "Design Consideration of New Six Degrees-of-Freedom Parallel Robots," Proceedings of the 1998 IEEE, International Conference on Robotics & Automation, Leuven, Belgium—May 1998—pp. 1327-1333.

Simaan, N. et al., "Geometric Interpretation of the Derivatives of Parallel Robots' Jacobian Matrix With Application to Stiffness Control," Journal of Mechanical Design, Mar. 2003, vol. 125, pp. 33-42.

Simaan, N. et al., "High Dexterity Snake-Like Robotic Slaves for Minimally Invasive Telesurgery of the Upper Airway," MICCAI2004, LNCS, pp. 17-24, 2004.

Simaan, N. et al., "Robot Construction for Surgical Applications," The 1st IFAC Conference on Mechatronic Systems, Darnstadt, Germany, pp. 553-558, 2000.

Simaan, N. et al., "Robotic Sugery of the Upper Airways: Addressing the Challenges of Dexterity Enhancement in Confined Spaces," Robotics in Surgery: History, Current and Future Applications, Editor: Russell A. Faust, pp. 261-280, 2007.

Simaan, N. et al., "Singularity Analysis of a Class of Composite Serial In-Parallel Robots," IEEE Transactions on Robotics and Automation, vol. 17, No. 3, Jun. 2001, pp. 301-311.

Simaan, N. et al., "Stiffness Synthesis of a Variable Geometry Planar Robot," Advances in Robot Kinematics, 463-472, 2002.

Simaan, N. et al., "Stiffness Synthesis of a Variable Geometry Six-Degrees-of-Freedom Double Planar Parallel Robot," The International Journal of Robotics Research 2003; 22; 757.

Simaan, N., "Task Based Design and Synthesis of Variable Geometry Parallel Robots," in Mechanical Engineering, vol. Ph.D., Haifa: Technion—Israel Institue of Technology, 2002 (abstract).

Stetter, Hans J., "Multivariate Polynomial Equations as Matrix Eigenproblems," WSSIAA 2 (1993) pp. 355-371.

Stewart, D., "A Platform witg Six Degrees of Freedom," Proc. Instn. Mech. Engrs. 1965-66, vol. 180, Pt. 1, No. 15, pp. 371-386.

Stoker, J.J., "Differential Geometry," Wiley-Interscience, 1969.

Suthakorn, J. et al., "A new inverse kinematics algorithm for binary manipulators with many actuators," Advanced Robotics, vol. 15, No. 2, pp. 225-244 (2001).

Suzumori, K. et al., "A Miniature Inspection Robot Negotiating Pipers of Widely Varying Diameter," Proceedings of the 2003 IEEE International Conference on Robotics & Automation, Taipei, Taiwan, Sep. 14-19, 2003.

Suzumori, K. et al., "Applying a Flexible Microactuator to Robotic Mechanisms," IEEE Control Systems, Feb. 1992, pp. 21-27.

Suzumori, K. et al., "Development of Flexible Microactuator and Its Applications to Robotic Mechanisms," Proceedings of the 1991 IEEE, International Conference on Robotics and Automation, Sacramento, California—Apr. 1991, pp. 1622-1627.

Suzumori, K. et al., "Flexible Microactuator for Miniature Robots," IEEE International Conference on Robotics and Automation, pp. 204-209, 1991.

Takahashi, M. et al., "The Development of an In-Pipe Microrobot Applying the Motion of an Earthworm," 5th International Symposium on Micro Machine and Human Science, pp. 35-40, 1994.

Thorne, M. et al., "Cochlear Fluid Space Dimensions for Six Species Derived From Reconstructions of Three-Dimensional Magnetic Resonance Images," Laryngoscope 109: Oct. 1999, pp. 1661-1668.

Tonini, R. et al., "Auditory steady-state response audiometry in profound SNHL: The impact of abnormal middle ear function," ENT—Ear, Nose & Throat Journal, May 2005, pp. 282-288.

Tsai, L-W. et al., "Solving the Kinematics of the Most General Six- and Five-Degree-of-Freedom Manipulators by Continuation Methods," Journal of Mechanisms, Transmissions, and Automation in Design, Jun. 1985, vol. 107, pp. 189-200.

Tsai, L. et al., "Robot Analysis: The Mechanics of Serial and Parallel Manipulators," John-Wiley & Sons, Inc., 1999.

Wakamatsu, H. et al., "Modeling of Linear Objects Considering Bend, Twist, and Extensional Deformations," IEEE International Conference on Robotics and Automation, 1995, pp. 433-438.

Wakamatsu, H. et al., "Static Analysis of Deformable Object Grasping Based on Bounded Force Closure," Proceedings of the 1996 IEEE International Conference on Robotics and Automation, Minneapolis, Minnesota—Apr. 1996, pp. 3324-3329.

Wakamatsu, H. et al., "The International Journal of Robotics Research," Static Modeling of Linear Object Deformation Based on Differential Geometry, The International Journal of Robotics Research 2004; 23; 293.

Walker, I.D. "Some Issues in Creating 'Invertebrate Robots," in the Proceedings of the International Symposium on Adaptive Motion of Animals and Machines, Montreal, Canada, pp. 1-6, 2000.

Walker, I.D. et al., "A Novel 'Elephant's Trunk' Robot," Proceedings of the 1999 IEEE/ASME, International Conference on Advanced Intelligent Mechantronics, Sep. 19-23, 1999, Atlanta, USA, pp. 410-415.

Wampler, C.W. "Solving the Kinematics of Planar Mechanisms by Dixon Determinant and a Complex-Plane Formulation," Journal of Mechanical Design, Transactions of the ASME, vol. 123, Sep. 2001, pp. 382-387.

Wampler. C.W. et al., "Numerical Continuation Methods for Solving Polynomial Systems Arising in Kinematics," Journal of Mechanical Design, Mar. 1990, vol. 112, pp. 59-68.

Wang, J. et al. "A Cochlear Electrode Array with Built-In Position Sensing," Engineering Research Center for Wireless Integrated MicroSystems, University of Michigan and Michigan Technological University, pp. 786-789, 2005.

Wang, J. et al., "A Parylene-Silicon Cochlear Electrode Array with Integrated Position Sensors," Proceedings of the 28th IEEE, EMBS Annual International Conference, New York City, USA, Aug. 30-Sep. 3, 2006, pp. 3170-3173.

Wang, J. et al., "A Thin-Film Cochlear Electrode Array With Integrated Position Sensing," Journal of Microelectromechanical Systems, vol. 18, No. 2, Apr. 2009.

Wang, J. et al., "An Integrated Position-Sensing System for a Mems-Based Cochlear Implant," Engineering Research Center for Wireless Integrated MicroSystems, pp. 1-3, 2005.

Wardrop, P. et al., "A temporal bone study of insertion trauma and intracochlear position of cochlear implant electrodes. I: comparison of Nucleus banded and Nucleus Contour electrodes," Hearing Research 203 (2005) 54-67.

Wei, W. et al., "A compact Two-armed Slave Manipulator for Minimally Invasive Surgery of the Throat," The first IEEE/RAS-EMBS International Conference on Biomedical Robotics and Biomechatronics (BIOROB'2006), Florida, USA, pp. 1-6, accepted for publication, 2006.

Wolf, A. et al., "A Mobile Hyper Redundant Mechanism for Search and Rescue Tasks," Proceedings of the 2003 IEEE/RSJ, Intl. Conference on Intelligent Robots and Systems, Las Vegas—Oct. 2003, pp. 2889-2895.

Wysocki, J. "Dimensions of the human vestibular and tympanic scalae," Hearing Research 135 (1999) 39-46.

Xu, K. et al., "Actuation Compensation for Flexible Surgical Snake-like Robots with Redundant Remote Actuation," Proceedings of the 2006 IEEE International Conference on Robotics and Automation, Orlando, Florida—May 2006, pp. 4148-4154.

Yoo, S.K. et al., "Three-Dimensional Geometric Modeling of the Cochlea Using Helico-Spiral Approximation," IEEE Transactions on Biomedical Engineering, vol. 47, No. 10, Oct. 2000, pp. 1392-1402.

Yoo, S.K. et al., "Three-Dimensional Modeling and Visualization of the Cochlea on the Internet," IEEE Transactions on Information Technology in Biomedicine, vol. 4, No. 2, Jun. 2000, pp. 144-151.

Zanganeh, K.E. et al., "The Inverse Kinematics of Hyper-Redundant Manipulators Using Splines," IEEE International Conference on Roboticd and Automation, pp. 2797-2802, 1995.

Zhang, J., Xu, K., Simaan, N., "A Pilot Study of Robot-Assisted Cochlear Implant Surgery Using Steerable Electrode Arrays," MICCAI' 2006 International Conference on Medical Image Computing and Computer-Assisted Intervention, Copenhagen, Sweden, pp. 33-40, 2006.

Zheng, Y.F. et al., "Strategies for Automatic Assembly of Deformable Objects," IEEE International Conference on Robotics and Automation, pp. 2598-2603, 1991.

Zlatanov, D. et al., "A Unifying Framework for Classification and Interpretation of Mechanism Singularities," Journal of Mechanical Design, Transactions of the ASME, vol. 117, Dec. 1995, pp. 566-572.

Zlatanov, D. et al., "Mechanical Design and Kinematic Analysis of a Three-Legged Six Degree-of-Freedom Parallel Manipulator," Robotics, Spatial Mechanisms, and Mechanical Systems DE vol. 45, pp. 529-536, 1992.

Merlet JP, "An Initiative for the Kinematic Study of Parallel Manipulators," Proceedings of the Workshop on Fundamental Issues and Futur Research Dorections for Parallel Mechanisms and Manipulators, 2002, pp. 2-9.

Lee TY and Shim JK, "Elimination-Based Solution Method for the Forward Kinematics of the General Stewart-Grough Platform" Computational Kinematics (CK2001), 2001, pp. 259-266.

Lee TY and Shim JK, "Improved dialytic elimination algorithm for the forward kinematics of the general Stewart-Gough Platform," Mechanism and Machine Theory 38 (2003) 563-577.

Lancaster, P. et al., Algebraic Riccati Equations: Oxford Science Publications, 1995, Preface and pp. 97-100.

Simaan, N. et al., "Minimally Invasive Surgery of the Upper Airways: Addressing the Challenges of Dexterity Enhancement on Confined Spaces," Nova Science Publications, 2005, pp. 261-280.

Burdick, J.W. et al., "The Kinematics of Hyper-Redundant Robots," The IMA Voluems in Mathematics and it Applications, ed. J. Baillieul, S. Sastry, and H. Sussmann, vol. 104, 1998: Springer-Verlag., pp. 61-90.

Juvinall, et al., Fundamentals of Machine Component Design Third Edition, John Wiley & Sons, 2000, pp. 773-776.

Rosheim, Mark E., Robot Evolution: The Development of Anthrobotics, John Wiley & Sons, Inc, 1994, pp. 112-113.

Shoham M, Goldberger S, Roffman M, Simaan N, Robot Structures for Surgery, First Israeli Symposium on Computer-Aided Surgery, Medical Robotics and Medical Imaging (ISRACAS'98), Technion City, Hafia, Israel, 1998.

* cited by examiner

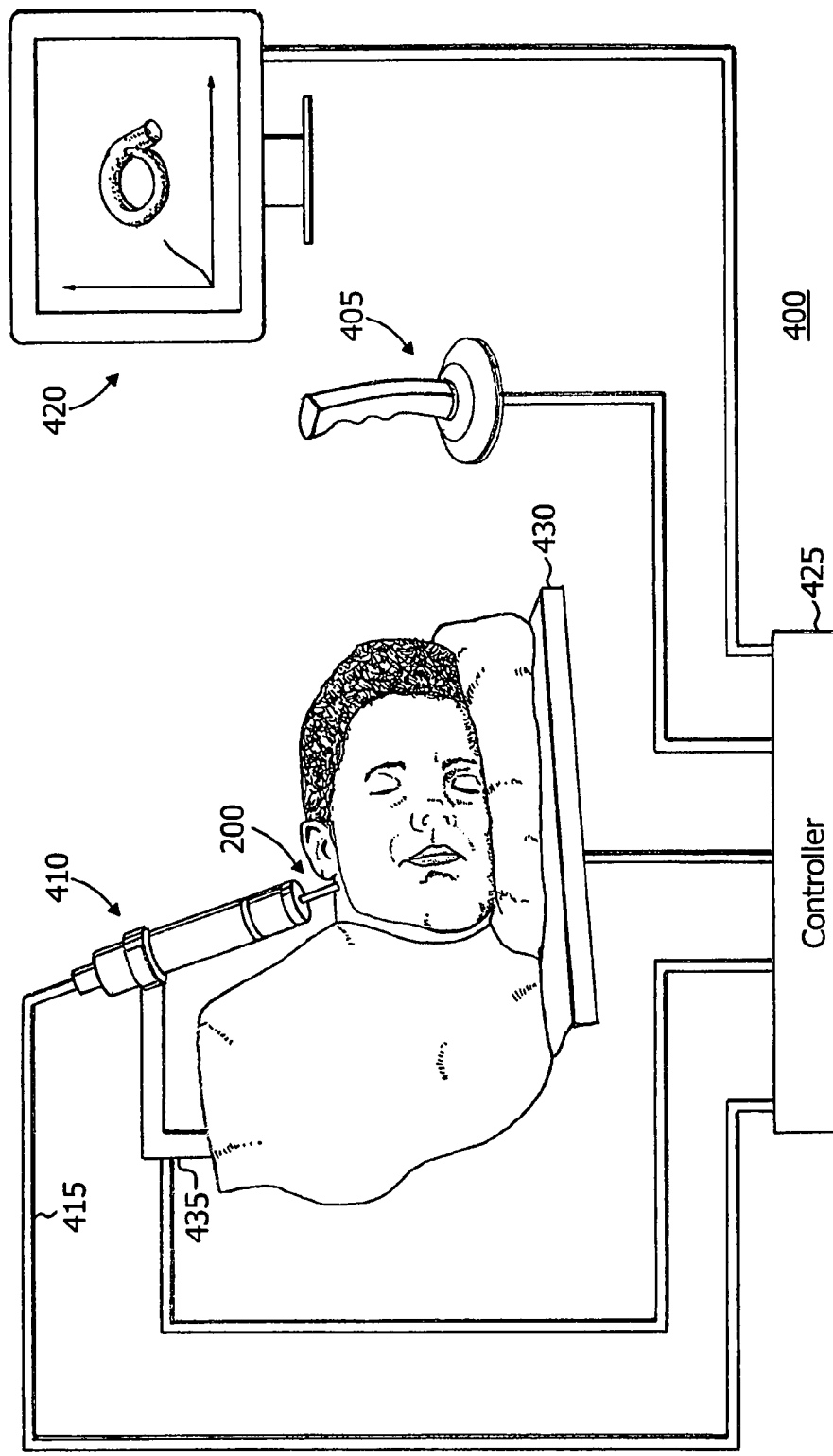

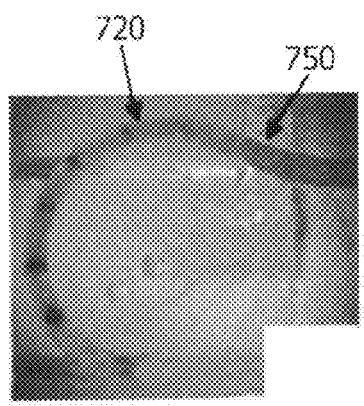
Fig. 7B(I)
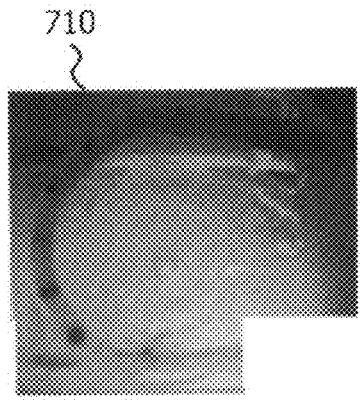
Fig. 7B(II)
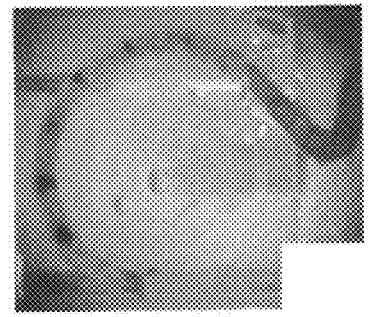
Fig. 7B(III)
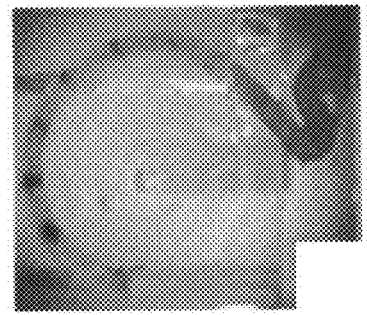
Fig. 7B(IV)
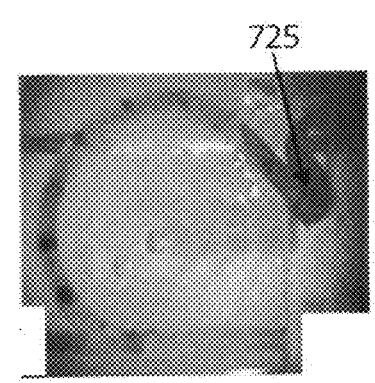
Fig. 7B(V)
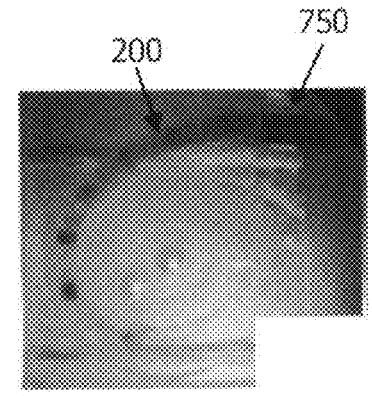
Fig. 7B(VI)

Fig. 7B(VII)

Fig. 7B(VIII)

Fig. 7B(IX)

ELECTRODE ARRAYS AND SYSTEMS FOR INSERTING SAME

CROSS-REFERENCE TO RELATED APPLICATION

This application claims the benefit of U.S. Provisional Patent Application No. 60/726,770, filed on Oct. 14, 2005, U.S. Provisional Patent Application No. 60/772,796, filed on Feb. 13, 2006, and U.S. Provisional Patent Application No. 60/781,994, filed on Mar. 13, 2006, which are hereby incorporated by reference herein in their entirety.

TECHNOLOGY AREA

The disclosed subject matter relates to electrode arrays and systems for inserting same.

BACKGROUND

Cochlear implants have been a major advent in the field of hearing repair. Cochlear implants have aided patients suffering from severe hearing loss due to damaged neuroepithelial cells of the inner ear. Typically, during cochlear implant surgery, a cochlear implant is placed under the skin in a small dimple carved in the mastoid bone. The implant comprises a receiver and a delicate, highly flexible beam called an electrode array that is inserted into the cochlea. The receiver receives (e.g., from an external microphone with a processor and a transmitter) and delivers the necessary excitation to the auditory nerve via the electrode array. In this way, the electrode array restores some sense of hearing by bypassing damaged neuroepithelial cells (hair cells) in the inner ear and directly providing electrical stimulation to the auditory nerve.

During insertion, the electrode array is usually inserted into the cochlea through a round window into the scala tympani channel. This surgery involves a high level of risk because injuring the basilar membrane can result in complete loss of residual hearing.

The success and applicability of cochlear implants are currently limited by several factors. For example, during cochlear implantation, electrode array insertion is performed "blindly," without controlling the interaction of the electrode array and cochlear duct. Also, for example, during implantation, the electrode array can buckle (e.g., from impacting the inner ear) and be rendered nonfunctional. Because of the risk, this surgery is typically performed on a limited subset of the population.

SUMMARY

In accordance with the disclosed subject matter, electrode arrays and systems for inserting same are disclosed.

In some embodiments, electrode arrays are provided, the electrode arrays comprising: a passive-bending portion; an active-bending portion coupled to the passive bending portion; at least one electrode located in at least one of the passive-bending portion and the active bending portion; and an actuator that causes the active-bending portion to deflect from the passive-bending portion.

In some embodiments, electrode arrays are providing, comprising: means for providing a passive-bending portion; means for providing an active-bending portion coupled to the passive bending portion; means for providing a plurality of electrodes located in at least one of the passive-bending portion and the active bending portion; and means for deflecting the active-bending portion from the passive-bending portion.

In some embodiments, electrode arrays configured for insertion into a cavity are provided, comprising: a body defining a long-axis and having a distal tip; and an actuator for deflecting the distal tip from the long axis.

In some embodiments, systems for inserting an electrode array in the body are provided, the systems comprising: an insertion module for controllably inserting the electrode array in the body and sensing forces applied to the electrode array; a monitor for providing information to a user; and a controller coupled to the insertion module and the monitor, wherein the controller causes the insertion module to control an amount of force that is applied to the electrode array.

In some embodiments, systems for inserting an electrode array in the body are provided, comprising: a means for controllably inserting the electrode array in the body and sensing forces applied to the electrode array; and a means, coupled to the insertion module and the monitor, for causing the means for controllably inserting to control an amount of force that is applied to the electrode array.

DESCRIPTION OF DRAWINGS

The disclosed subject matter will be apparent upon consideration of the following detailed description, taken in conjunction with accompanying drawings, in which:

FIG. 4A is a depiction of a system for inserting an electrode array in accordance with some embodiments of the disclosed subject matter;

DETAILED DESCRIPTION

In accordance with the disclosed subject matter, electrode arrays and systems for inserting same are disclosed.

In some embodiments, an active-bending electrode array can be inserted in the cochlea to restore hearing loss. As described in more detail below, in some embodiments, force can be applied to an actuation thread in the active-bending electrode array creating a deflection in an active-bending electrode array. In some embodiments, magnetic forces may be used to create a deflection in an active-bending electrode array. This deflection can assist the surgeon in implanting an active-bending electrode array in the cochlea and minimize buckling of the electrode array. In some embodiments, a system can be used to insert an electrode array (whether an active-bending electrode array or a passive-bending electrode array) in the cochlea. The system allows a surgeon to visualize the delivery of electrode array into the cochlea. For example, the surgeon can monitor forces applied on an electrode array during insertion to insure that the inner ear is not injured and the electrode array does not buckle.

Figure 1:
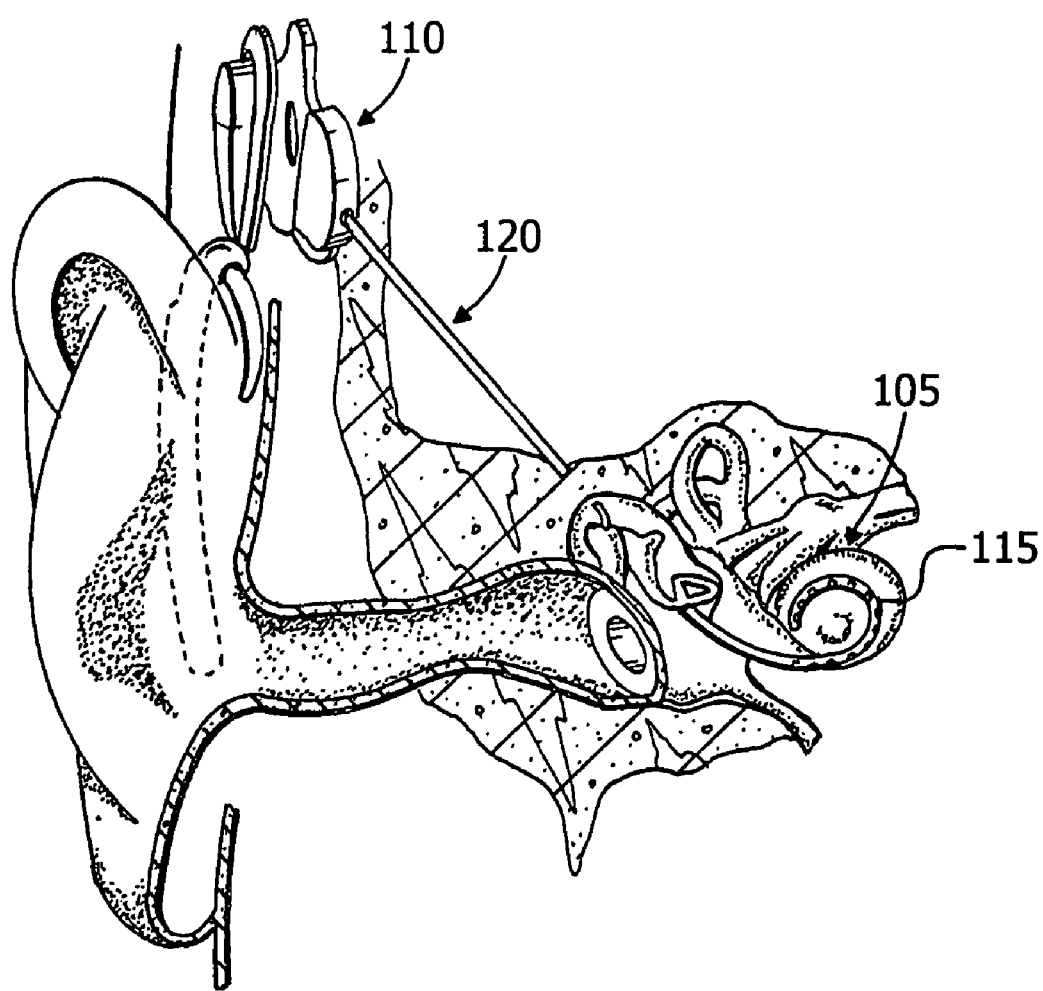
FIG. 1 is an anatomical depiction of a human ear and cochlear implant in accordance with some embodiments of the disclosed subject matter.

Referring to FIG. 1, an anatomical depiction of the human ear is displayed. It will be apparent that the disclosed subject matter can be used in other parts of the body (e.g., the lungs, heart, kidneys, fetus, etc.). For ease of understanding, this application primarily focuses on electrode arrays implanted in the inner ear 105. In some instances, a device 110 (e.g., transmitter, receiver, microphone, or processor) can be implanted under skin in a dimple carved into the mastoid bone and attached to an electrode array 115 located in inner ear 105 by a wire connection 120. For ease of reference, the inner ear shall refer to the cochlea, vestibule, and semi-circular canals.

Figure 2:
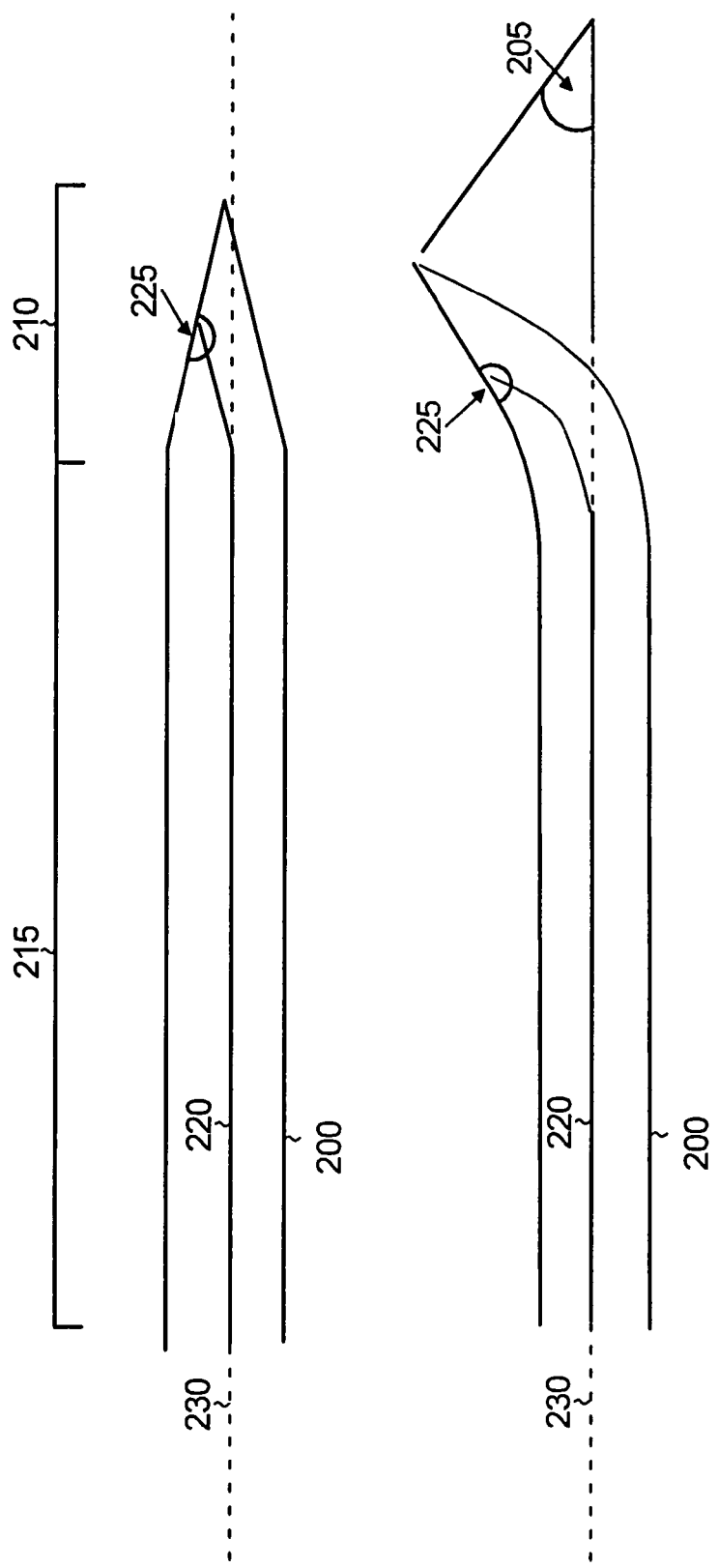
FIG. 2 is a side, cross-sectional view drawing illustrating an active-bending electrode array in accordance with some embodiments of the disclosed subject matter.

Referring to FIG. 2, two illustrations of an active-bending electrode array 200 that can be used in various embodiments are shown. In some instances, active-bending electrode array 200 can comprise multiple portions, such as an active-bending portion 210 and a passive-bending portion 215. Active-bending electrode array 200 can also comprise an actuation thread 220, a bounding portion 225, and a plurality of electrodes (not shown). The electrodes, for example, may comprise any suitable number of electroides and may be positioned at any suitable location in the electrode array.

As shown, actuation thread 220 is located inside active-bending portion 210 and passive-bending portion 215. Further, actuation thread 220 can attach to active-bending portion 210 at bounded portion 225. Bounded portion 225 can attach actuation thread 220 to active-bending portion 210 using an adhesive (cyanoacrylates, polymer adhesives, etc.) or other means (melting, stitching, etc.). As shown, in some instances, actuation thread 220 can pass through passive-bending portion 215 along centerline 230 and, as actuation thread 220 passes through active-bending portion 210, actuation thread 220 diverges from centerline 230. In some instances, actuation thread 220 can pass through passive-bending portion 215 off of centerline 230. For example, actuation thread 220 can pass through passive-bending portion 215 at some distance away from centerline 215. In some embodiments, actuation thread 220 can pass through passive-bending portion 215 at an angle that is not parallel to centerline 230.

Active-bending portion 210 can deflect (e.g., from its resting configuration) when tension is applied to actuation thread 220. In some instances, passive-bending portion 215 can also deflect when tension is applied to actuation thread 220. For example, tension applied to actuation thread 220 may impart force on active-bending portion 210 causing active-bending portion 210 to deflect. In some embodiments, lessening the tension on actuation thread 220 returns active-bending portion 210 to its resting configuration. As shown in the bottom half of FIG. 2, active-bending electrode array 200 can arc by an angle 205 when tension is applied to actuation thread 220. This angle 205 can assist surgeons during surgery, reducing damage to the body (e.g., the inner ear), and reducing damage to the active-bending electrode array (e.g., lessen the chances for buckling).

In some instances, a plurality of electrodes can be located within an active-bending electrode array. Electrodes located in active-bending electrode array 200 can comprise platinum or any other material deemed suitable. In some instances, electrodes located within active-bending electrode array 200 are in a location where they contact the inner ear. For example, the surface of an active-bending electrode array can have holes (e.g., pores, dimples, cut outs, etc.) where electrodes can touch the inner ear of a patient. That is, the electrodes may remain flush with the surface of an active-bending electrode array or they may extend beyond the surface of an active-bending electrode array (e.g., dimple out). In other instances, electrodes located within active-bending electrode array 200 can be in a location where they do not contact the inner ear of a patient. For example, the electrodes can be fully embedded in the active-bending electrode array. The electrodes in electrode array can be electrically coupled to any suitable device, such as device 110 of FIG. 1.

In some instances, both active-bending portion 210 and passive-bending portion 215 comprise a substantially similar material. For example, active-bending portion 210 and passive-bending portion 215 can comprise a flexible material (e.g., silicon rubber, plastic, urethane, etc.). In other instances, the properties of active-bending portion 210 and passive-bending portion 215 are substantially different. For example, passive-bending portion 215 can comprise a material that is substantially more rigid than active-bending portion 210. This can be done, for example, to increase the ability to push active-bending electrode array while still allowing a substantial deflection in active-bending portion 210.

In some instances, actuation thread 220 can be a single uniform material. For example, actuation thread 220 can be constructed of a Kevlar thread with a diameter of about 10 um. In other instances, the properties across the length of actuation thread 220 can vary. That is, actuation thread 220 can have different properties depending on where it is located in an active-bending electrode array. It will be understood that actuation thread 220 can be a substantially solid material exhibiting a uniform cross section (e.g., circular, hollow, square, rectangular, star shaped, etc.). Further, actuation thread 220 can comprise more than one material. For example, actuation thread 220 can be a braid or weave of more than one material. Actuation thread 220 can comprise any suitable material, such as a natural material (cotton, silk, etc.), synthetic material (nylon, Teflon, etc.), metallic material (carbon, NiTi, etc.), or any other suitable material. In some instances, more than one actuation thread can be used in an active-bending electrode array.

In some embodiments, active-bending electrode array 200 can have a substantially consistent shape and can have a substantially smooth outer surface. In some embodiments, variations in the shape and/or the outer surface of active-bending electrode array 200 can change the properties of active-bending electrode array 200. For example, active-bending electrode array 200 can include surface variations (e.g., pits or grooves) or varying thickness (e.g., thinned in the active-bending portion) thereby concentrating stress at a specific location. This concentrated stress can provide enhanced control over angle 205 when force is applied.

In some instances, bonding portion 225 can be located near a distal end of active-bending electrode array 200. Bonding portion 225 alternatively can be located at any other location or set of locations.

In some embodiments, a magnet and a magnetic steering device can be used to create angle 205. For example, a magnetic stylet may be located within array 200, and a magnetic steering device may include controller-controlled electromagnets. Steering can be accomplished utilizing the intrinsic properties of magnets (e.g., like charges repel, opposite charges attract, etc.). One or more magnets can be located at different locations in an active-bending electrode array. Bonding portion 225 can bond a magnet to an active-bending electrode array. Any material that reacts with a magnet (e.g., ferrous materials) can be used instead of a magnet in suitable circumstances. In some instances, a magnet can be permanently bonded in an active-bending electrode array. In other instances, a magnet can be temporarily bonded in an active-bending electrode array. For example, after an active-bending electrode array is placed in a patient the surgeon can remove the magnet (e.g., by pulling on a thread attached to the magnet).

Figure 3:
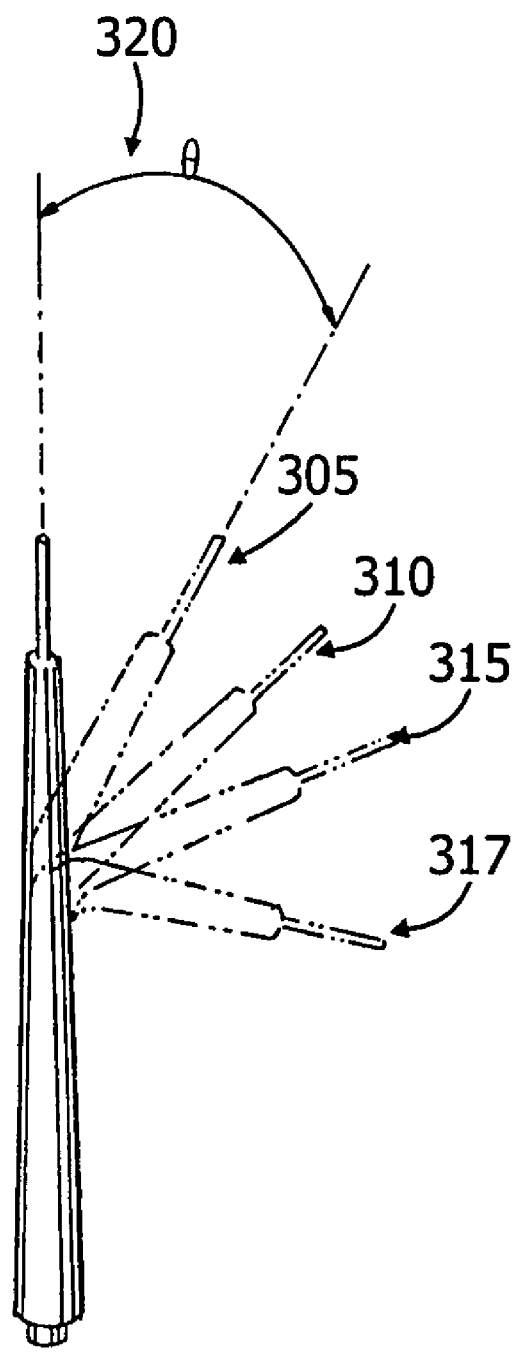
FIG. 3 demonstrates an active-bending electrode array during various ranges of deflection in accordance with some embodiments of the disclosed subject matter.

Referring to FIG. 3, in some embodiments, actuation thread 220 (not shown) can allow an active-bending electrode array 200 to deflect various amounts. As shown, applying tension to actuation thread 220 (not shown) can create a substantial deflection in active-bending electrode array 200 as is illustrated by deflections 305, 310, 315 and 317. As shown, in some embodiments, various angles of deflection 320 may be possible. For example, angles of deflection 320 may be in excess of 360 degrees in some embodiments.

Referring to FIG. 4A, in some embodiments, a system 400 can be used for inserting an electrode array (e.g., an active-bending electrode array or a passive-bending electrode array). System 400 can comprise an input device 405, an insertion module 410, a data connection 415, a controller 425, and a monitor 420. System 400 can also include a table 430 that allows motion in one or more directions (e.g., motion in a positive or negative direction along one or more orthogonal axes). In some embodiments, an arm 435 can connect insertion module 410 with table 430. In some embodiments, arm 435 can be robotic.

In use, insertion module 410 can be placed near the site of entry into the body (e.g., the ear canal, incision point, etc.). In some instances, insertion module 410 can sit on table 430 that is also located near the site of entry into the body. In some embodiments, insertion module 410 may be attached to a patient's head using a stereotactic frame or any other suitable mechanism. Using input device 405, the user can steer insertion module 410 into and inside the body. Insertion module 410 can then advance an electrode array into the body. While advancing, insertion module 410 can receive force and location measurements on the electrode array from sensors in insertion module 410. Force and location measurements can be displayed to the user on monitor 420. If an active-bending electrode array is used, controller 425 can deflect the active-bending electrode array by applying force (e.g., tension on an actuation thread) to the active-bending electrode array. When the electrode array is in a desirable position, insertion module 410 can be removed from the body leaving the electrode array in the body. In some embodiments, the angle of approach and deflection of an electrode array can be controlled by a path-planning module in controller 425, while the depth of insertion can be controlled through input device 405 by the user.

In some embodiments, insertion module 410 can reduce frictional forces on an electrode array by vibrating the electrode array. For example, insertion module 410 can vibrate an electrode array to decrease frictional forces as the electrode array traverses the inner ear. In some instances, vibration in insertion module 410 is a periodic oscillation, aperiodic oscillation, or a combination of both periodic and aperiodic oscillations.

In some instances, vibration can be sensed by at least one sensor in system 400 and a counteractive force created by an at least one actuator located in insertion module 410.

In some embodiments, insertion module 410 can move in many directions. For example, insertion module 410 can have six-axis motion. Six-axis motion in insertion module 410 can be provided by a six-axis miniature parallel system. Further, insertion module 410 can have at least one sensor (e.g., an ATI Nano 17 U-S-3 six-axis force sensor produced by ATI Industrial Automation located in Apex N.C.) for measuring force (e.g., force applied to an electrode array).

In some embodiments, system 400 guides an under-actuated active-bending electrode array. That is, system 400 has fewer actuators than degrees-of-freedom that can be controlled.

In some embodiments, rather than delivering an active-bending electrode array, system 400 delivers a passive-bending electrode array into the body. A passive-bending electrode array deflects when an external force (e.g., impacting tissue in the body) is applied to it.

In some embodiments, system 400 can incorporate a magnetic guidance system. In these embodiments, an active-bending electrode array comprises an active-bending portion, a passive-bending portion, and a magnet or a magnetic material. In some instances, there may be no actuation thread in the active-bending electrode array. A magnetic guidance system can be located external to the body. In some instances, a magnetic guidance system can be attached to insertion module 410. A magnetic guidance system can incorporate electro magnets. When a deflection is desired, the system can apply magnetic force to an active-bending electrode array and produce a deflection similar to that seen when force is applied by an actuation thread. In some instances, a magnet can be attached (e.g., by a thread) to insertion module 410. When desired, insertion module 410 can apply force and remove the magnet from the active-bending electrode array.

In some embodiments, input device 405 can incorporate force feedback. When force is detected on an electrode array (e.g., a force detected by an active-bending electrode array connected to the parallel robot through a small ATI Nano17 U-S-3 six-axis force sensor) force can be applied by input device 405 (e.g., Sidewinder Force Feedback™ from Microsoft Co., Impulse Stick from Immersion Corporation, etc.) to the user. For example, as force applied to an active-bending electrode array increases, input device 405 can vibrate or provide resistance with increasing strength indicating the situation to the surgeon.

In some embodiments, the surgeon controls the motion of the insertion module in all directions using the input device and relies on information displayed on monitor 420. For example, the surgeon can deliver an electrode array into the body and determine the safety of insertion based on, for example, the insertion force measurements provided on monitor 420 based on force feedback.

In some embodiments, the surgeon controls the insertion module in the axial direction during insertion while a controller 425 steers all other directions. In some instances, the controller, for example, has a preset path-planning module. In some instances, the preset path-planning module is based on, for example, 3D extensions of a 2D template of a cochlea. In some instances, using a path-planning module, the forces on the electrode array are reduced during insertion. In some instances, the surgeon controls the speed of the insertion (e.g., via the input device) while the controller controls the orientation of insertion and the bending of the electrode (e.g., using the insertion module).

In some embodiments, system 400 can perform the insertion automatically while offering the surgeon the possibility to take control. For example, the system may deliver an electrode array by following a path-planning module based on patient data.

Figure 5A:
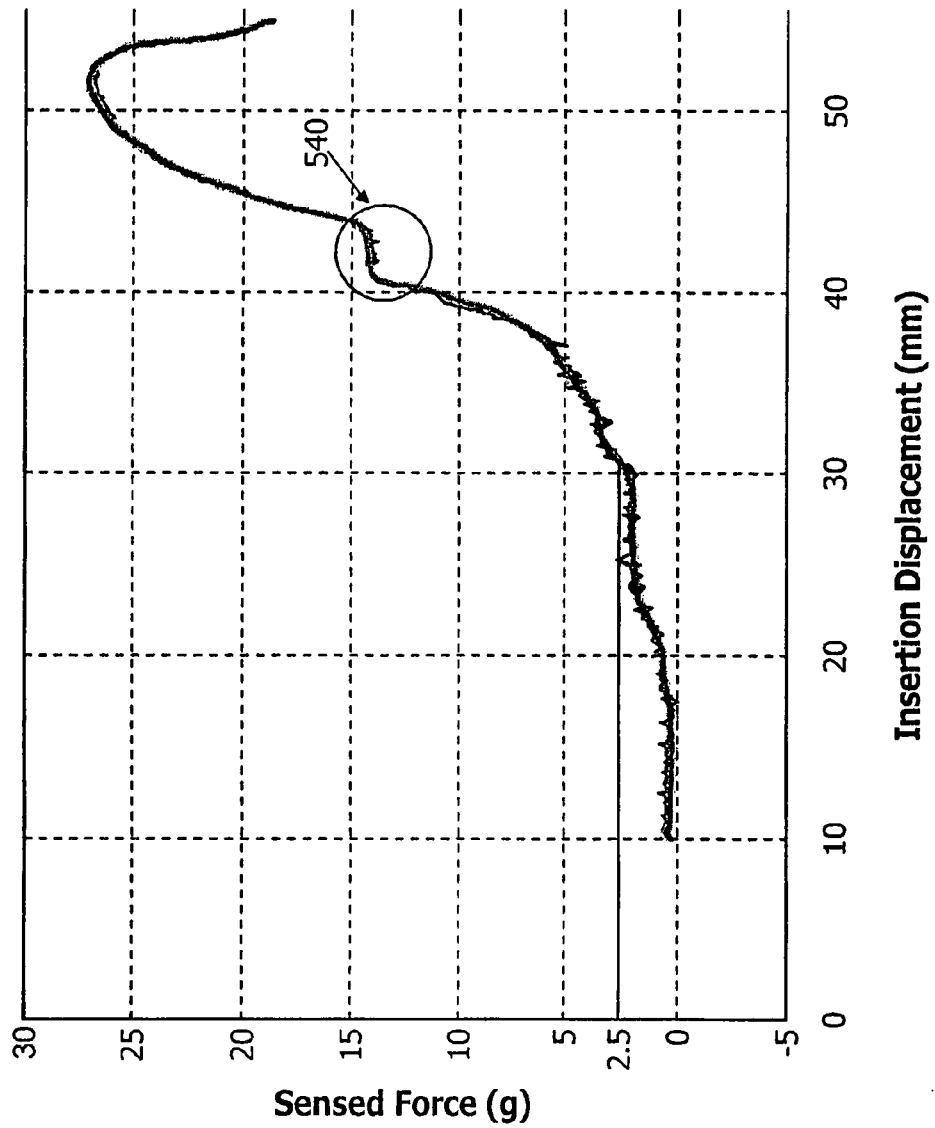
FIGS. 5A-5D are graphs that can be presented during insertion of an electrode array in accordance with some embodiments of the disclosed subject matter.
Figure 5B:
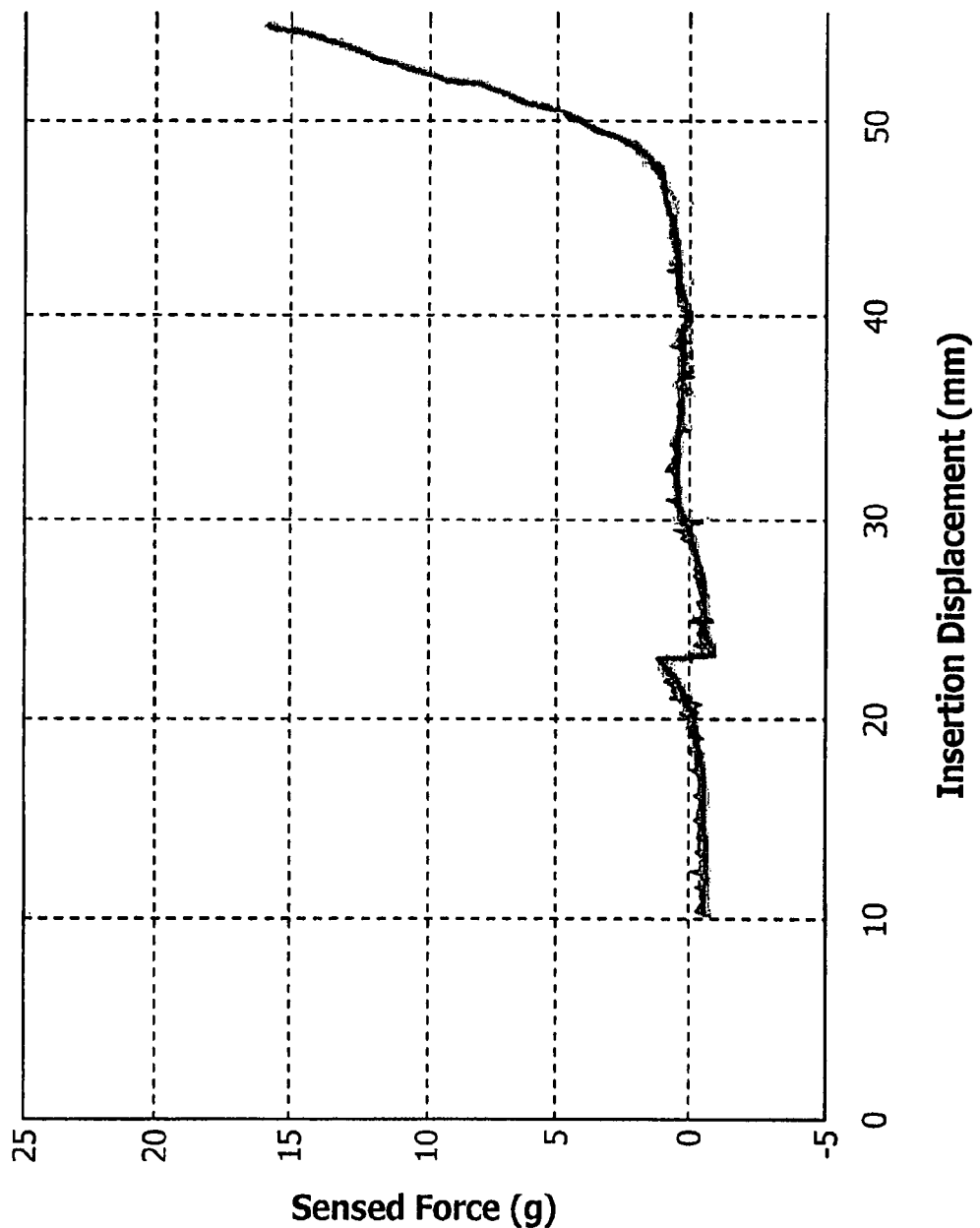

In some embodiments, monitor 420 can display the location of the active-bending electrode array in the body (e.g., the inner ear) and can also display a graph of the force being applied to the active-bending electrode array (e.g., as illustrated in FIGS. 5A and 5B). In some instances, a single line in the graph can demonstrate all forces applied to an active-bending electrode array. In other instances, multiple lines in the graph can display various forces applied to an active-bending electrode array. For example, one line in the graph can display external forces (e.g., force from contacting the body) applied on an active-bending electrode array and another line can display the force applied by an actuation thread.

For example, as shown in FIG. 5A, in some embodiments, monitor 420 displays the force applied on a passive-bending electrode array with respect to insertion distance in the body. For example, at an insertion displacement (i.e., the distance the electrode array has been inserted into the body) of 30 mm (e.g., 30 mm from the point of entry into the body) the sensed force on the passive-bending electrode array is 2.5 grams. In some instances, an electrode array may buckle. Buckled electrode arrays may be displayed on monitor 420 as a substantial peak in force and/or flat line. For example, area 540 indicates a buckled passive-bending electrode array.

Referring to FIG. 5B, in some embodiments, monitor 420 displays the force applied on an active-bending electrode array with respect to the insertion distance in the body. For example, at an insertion displacement of 50 mm the sensed force on the active-bending electrode array is 5 grams.

Figure 5C:
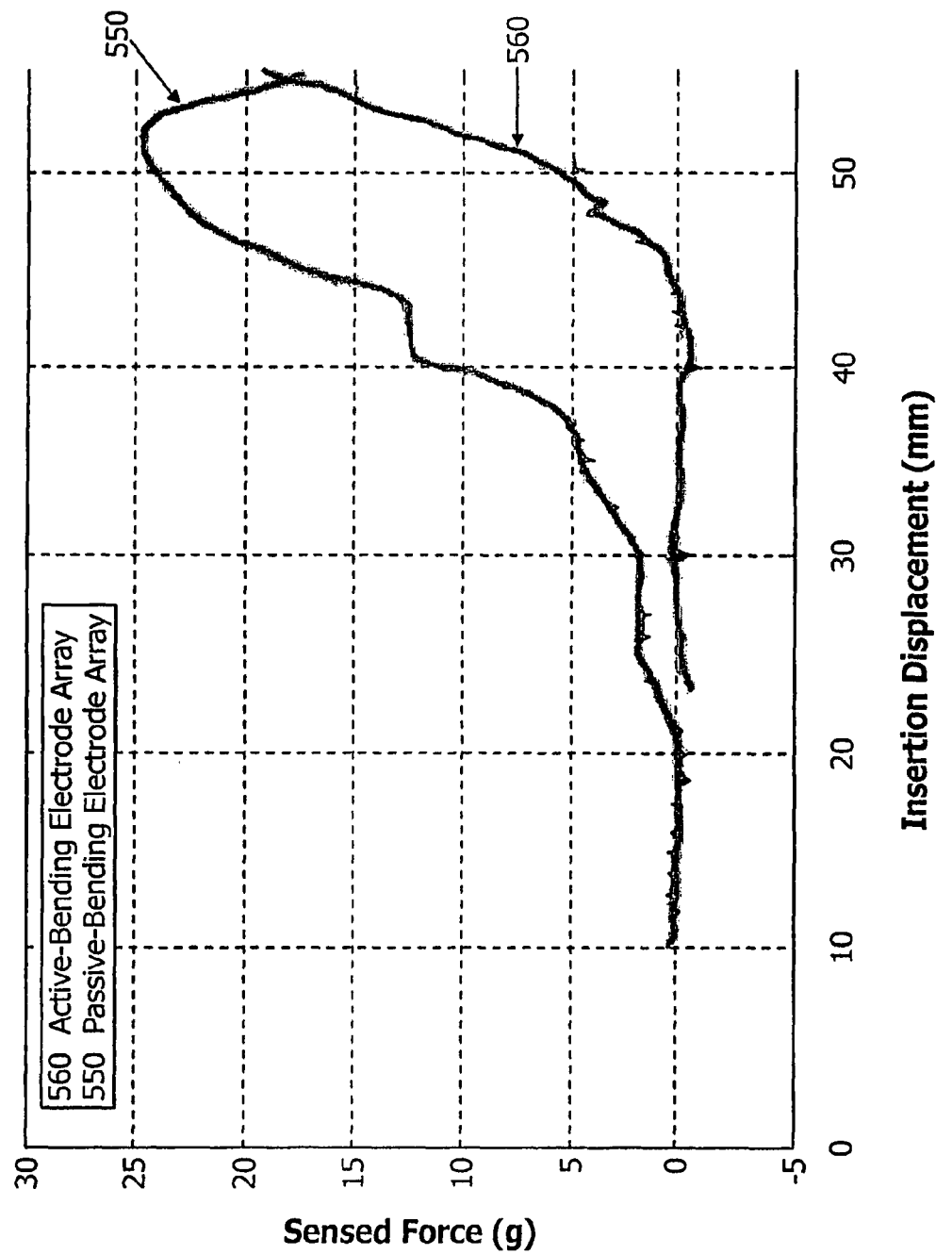

Referring to FIG. 5C, in some embodiments, monitor 420 displays more than one plot of forces applied on an electrode array (e.g., active-bending electrode array plot 560 and passive bending electrode array plot 550). For example, force measurements can be stored and displayed on monitor 420 thereby aiding a surgeon in determining if the force on the electrode array is beyond an acceptable limit. In some instances, force measurements displayed against insertion distances can be used to determine how to bend an active-bending electrode array at various insertion depths. For example, if increased force is observed at a certain depth, this can indicate to the surgeon that a deflection is required.

Figure 5D:
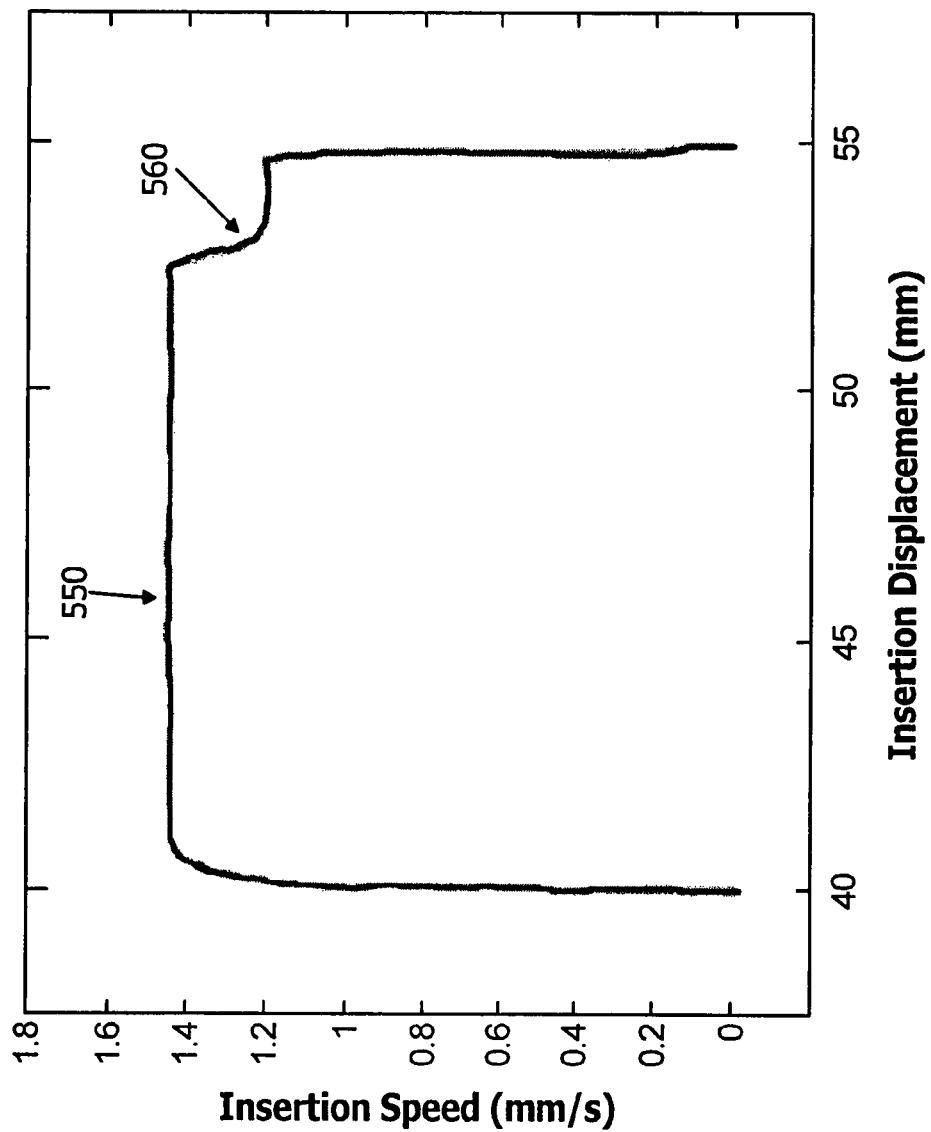

Referring to FIG. 5D, in some embodiments, monitor 420 displays insertion speed of an electrode array with respect to insertion distance. For example, the insertion speed displayed against insertion displacement can be for an active-bending electrode array. As shown, in some embodiments, the insertion speed may remain substantially constant (e.g., constant region 550). In other embodiments, the insertion speed may change at various depth of insertion (e.g., variable region 560).

It will be understood that monitor 420 can display any form of information (e.g., forces, temperature, time, velocity, acceleration, vibration, etc.) to the surgeon related to an electrode array insertion (e.g. delivering, positioning, etc.).

Referring back to FIG. 4B, in some embodiments, a surgeon 505 can guide the insertion of an electrode array without using an insertion module 410 or input device 405. Rather, the surgeon 505 can use an insertion module 450. Like insertion module 410, insertion module 450 can be used to insert an electrode array into the cochlea. In some embodiments, insertion module 450 can compensate for external forces. For example, input module 450 can compensate for tremors in the surgeon's hand using suitable motion sensors and actuators. External forces (e.g., tremors in the surgeon's hands) can be detected by a sensor, a digital processing device can determine the corrective force needed, and an insertion module can produce the corrective force to compensate for the external force. External force compensation can be as simple as, for example, detecting an external force and applying an equal and opposite force to counter the external force. However, external force compensation can be significantly more complex, for example, analyzing the external force and comparing the force to a range of allowable forces. If the external force falls outside an acceptable range of allowable force, the force compensation system can cancel out the force. Force cancellation can involve not simply a single equal and opposite force, but, rather, for example, it can require a series of small forces compensating for the larger external force.

Figure 4B:
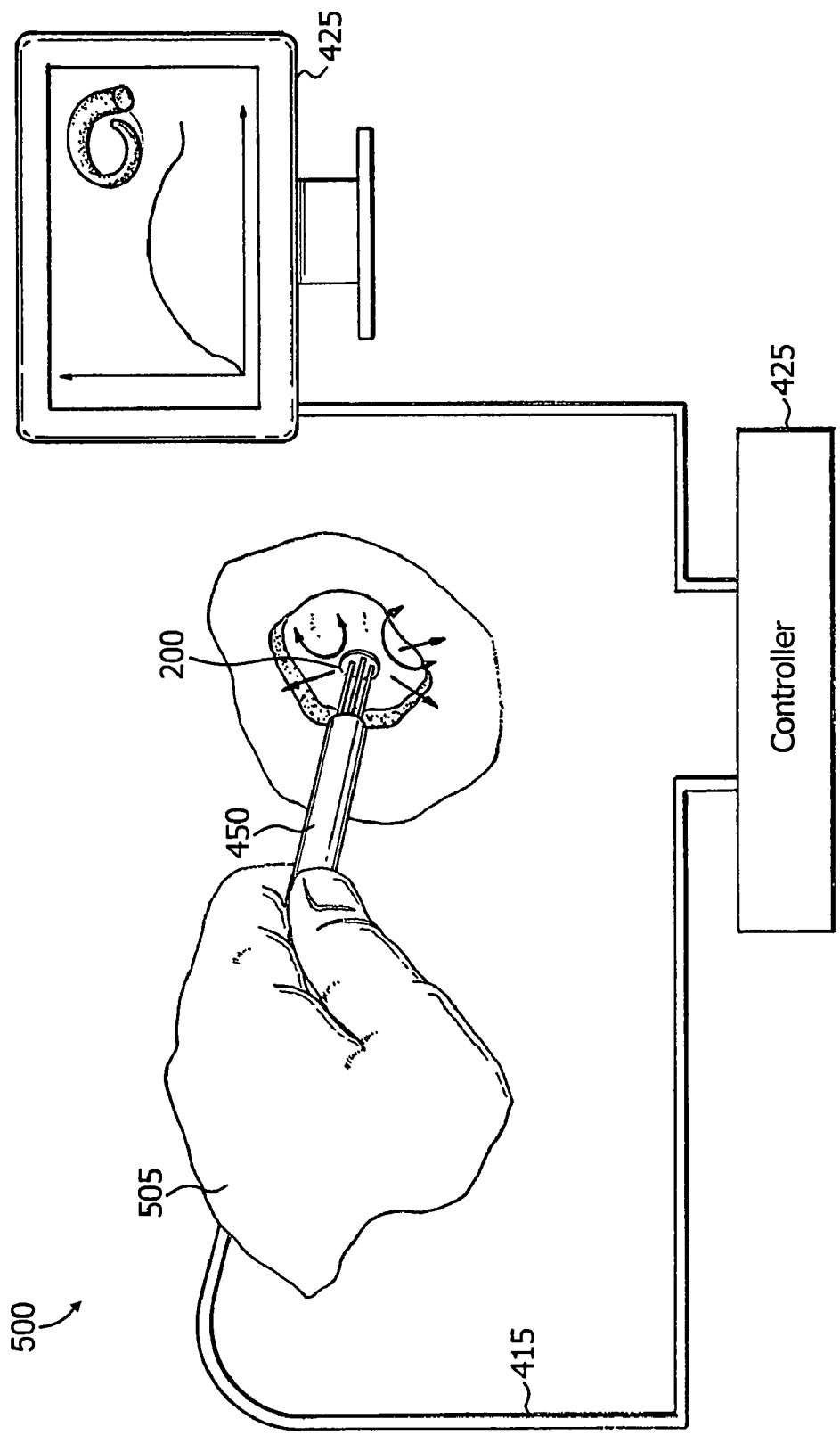
FIG. 4B is a depiction of another system for inserting an electrode array in accordance with some embodiments of the disclosed subject matter.

Controller 450 may be any suitable device or devices for receiving input from and controlling the operation of input device 405, insertion modules 410 and 450, arm 435, table 430, and monitor 420 illustrated in FIGS. 4A and 4B. For example, controller 450 may be a general-purpose computer, including a digital processing device, with suitable interface cards.

Figure 6:
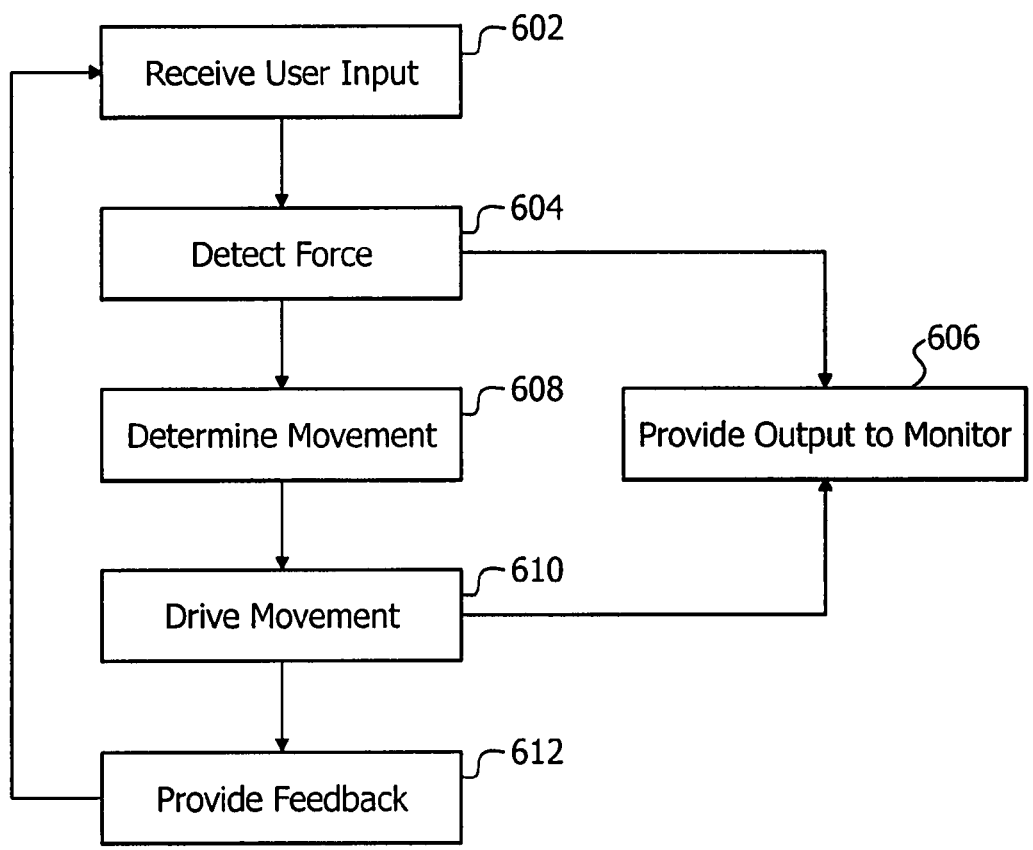
FIG. 6 is a diagram of a process for controlling systems for inserting an electrode array in accordance with some embodiments of the disclosed subject matter.

Turning to FIG. 6, a diagram of a process 600 that can operate in controller 425 is illustrated. As shown, process 600 can receive user input at 602. This user input may be provided from user input device 405 or insertion module 450, and may include hand movements (whether intentional or unintentional), button depressions, etc. At 604, process 600 can detect forces applied on an electrode array. These forces may be detected by insertion module 410 or 450 as described above. At 608, process 600 can determine the movement required of insertion module 410 or 450. This movement can include movement to insert the electrode array, bend the electrode array, remove insertion module 410, remove hand tremors from insertion module 450, move arm 435, move table 430 or any other movement associated with insertion module 410, arm 435, table 430, and insertion module 450. The movement determined by 608 can include movement calculated by a path-planning module as described herein. At 610, process 610 may drive the movement of insertion module 410, arm 435, table 430, and insertion module 450. The drive signals may be generated by a suitable interface in controller 450. The force detected at 604 and the movement driven at 610 can be used to provide an output to monitor 420 at 606. At 606, process 600 can additionally or alternatively generate any other suitable output to monitor 420 as described herein. At 612, process 600 may provide feedback to a user, such as by creating force on a joystick being used by the user, as described above. Process 600 may then loop back to 602. While the blocks of process 600 are illustrated in FIG. 6 as occurring in a specific order, it should be apparent to one of skill in the art that these blocks may occur in any suitable order or in parallel.

Figure 7A:
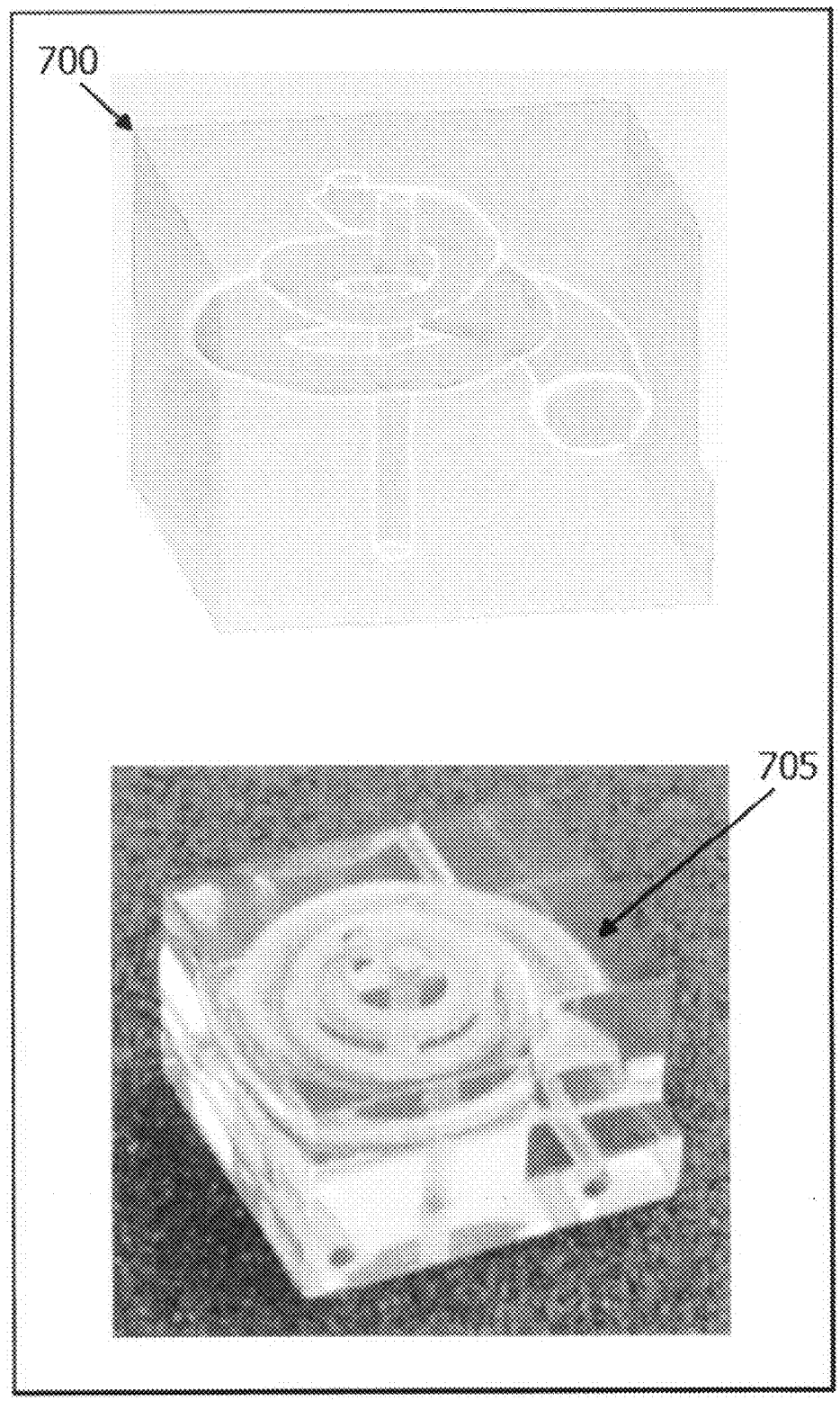
FIGS. 7A-7C displays various models of a cochlea in accordance with some embodiments of the disclosed subject matter.

Referring to FIG. 7A, in some embodiments, a 3D model can be used to simulate surgery. For example, as displayed, a computer model 700 of a cochlea can be produced using Computer-Aided Design (CAD) tools. Using stereo-lithography, computer model 700 can be used to create a prototype model 705 of a cochlea. Further, the prototype model can be used to create a 3D model for performing simulated surgery (e.g., practicing using a system for inserting an active-bending electrode array).

Figure 7B:
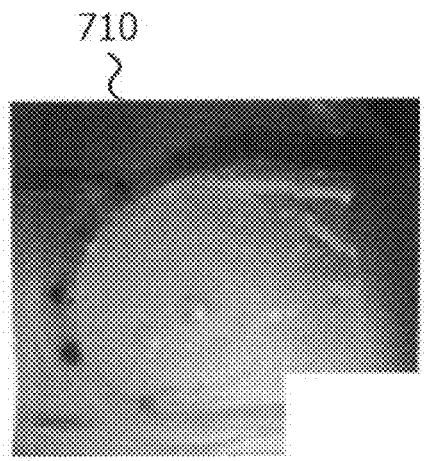
Figure 7B:
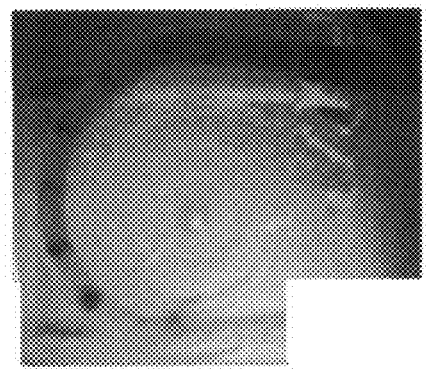
Figure 7B:
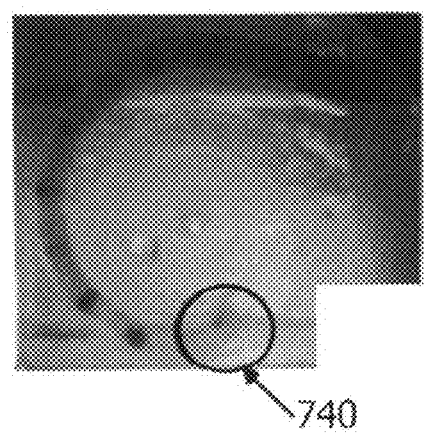
Figure 7B:
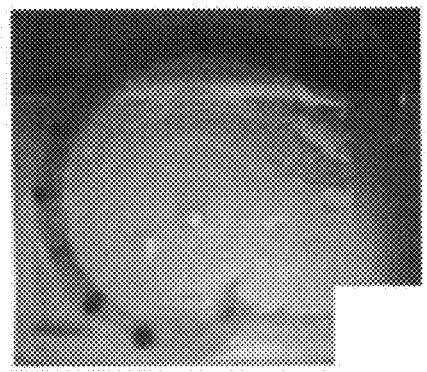

Referring to FIG. 7B, in some embodiments, an electrode array (i.e., an active-bending electrode array 200 or a passive-bending electrode array 720) may be delivered into a cochlea model 710 (e.g., delivered into cochlea model 710 at an insertion point 750). For example, cochlea model 710 can be used to facilitate teaching doctors how to deliver active-bending electrode array 200 and passive-bending electrode array 720 into a cochlea. Experiments performed on cochlea models can, for example, establish better deflections for active-bending electrodes and help to eliminate frictional forces applied to an electrode array during delivery. It will be understood that frictional forces applied to an electrode array may buckle the electrode array. For example, as shown in slides I-V, passive-bending electrode array 720 can be inserted into cochlea model 710, however, prior to completing the first 180 degrees, passive-bending electrode array 720 buckles as shown in area 725. Referring to steps VI-X active-bending electrode array 200 enters into cochlea model 710 and completes the first 180 degrees without buckling. Referring to step IX, active-bending electrode array 200 creates a deflection 740. In some embodiments, deflection 740 allows active-bending electrode array 200 to be delivered into a cochlea without buckling. In some embodiments, a cochlea model may be placed in a human skull model. For example, this may be done to provide the surgeon with a more realistic training environment.

Figure 7C:
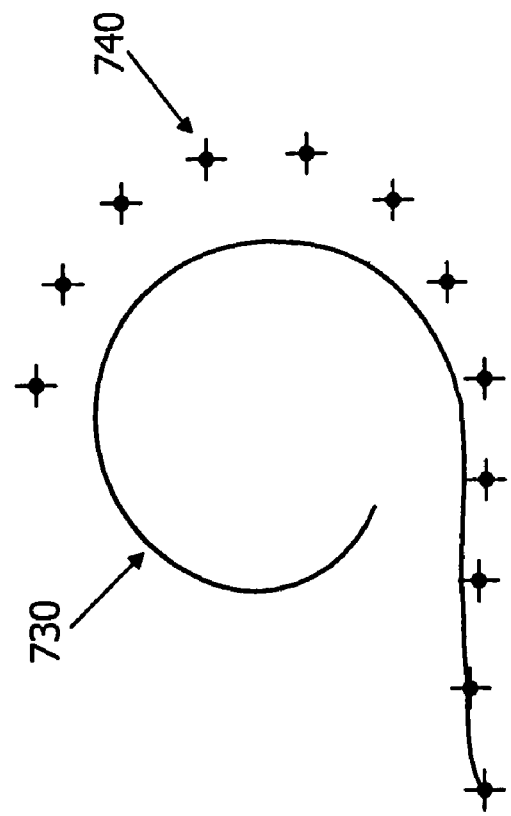
Figure 7C:
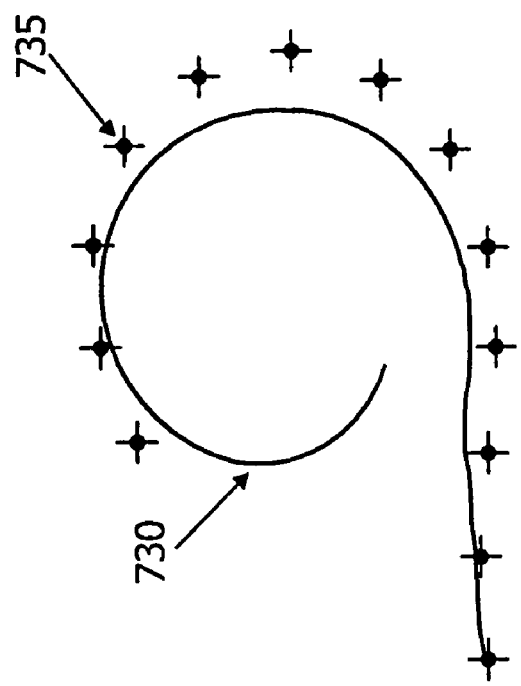

Referring to FIG. 7C, in some embodiments, an active-bending electrode array can shape (e.g., curve, bend, etc.) at least partially to the anatomy of the cochlea. For example, the shape of the cochlea can be displayed as a cochlea curve 730, the shape of an active-bending electrode array delivered into the cochlea can be displayed as an active-bending electrode array curve 735, and the shape of a passive-bending electrode array delivered into the cochlea can be displayed as a passive-bending electrode array curve 740. As shown, for example, active-bending electrode array curve 735 more accurately adheres to cochlea curve 730 than passive-bending electrode array curve 740. In some embodiments, for example, an active-bending electrode array delivered into the cochlea more accurately follows the curvature of the cochlea and generates less frictional forces than a passive-bending electrode array. In some embodiments, the active-bending electrode array more accurately adheres to the curvature of a cochlea than a passive-bending electrode array because, for example, the active-bending electrode array can create an deflection.

Figure 8:
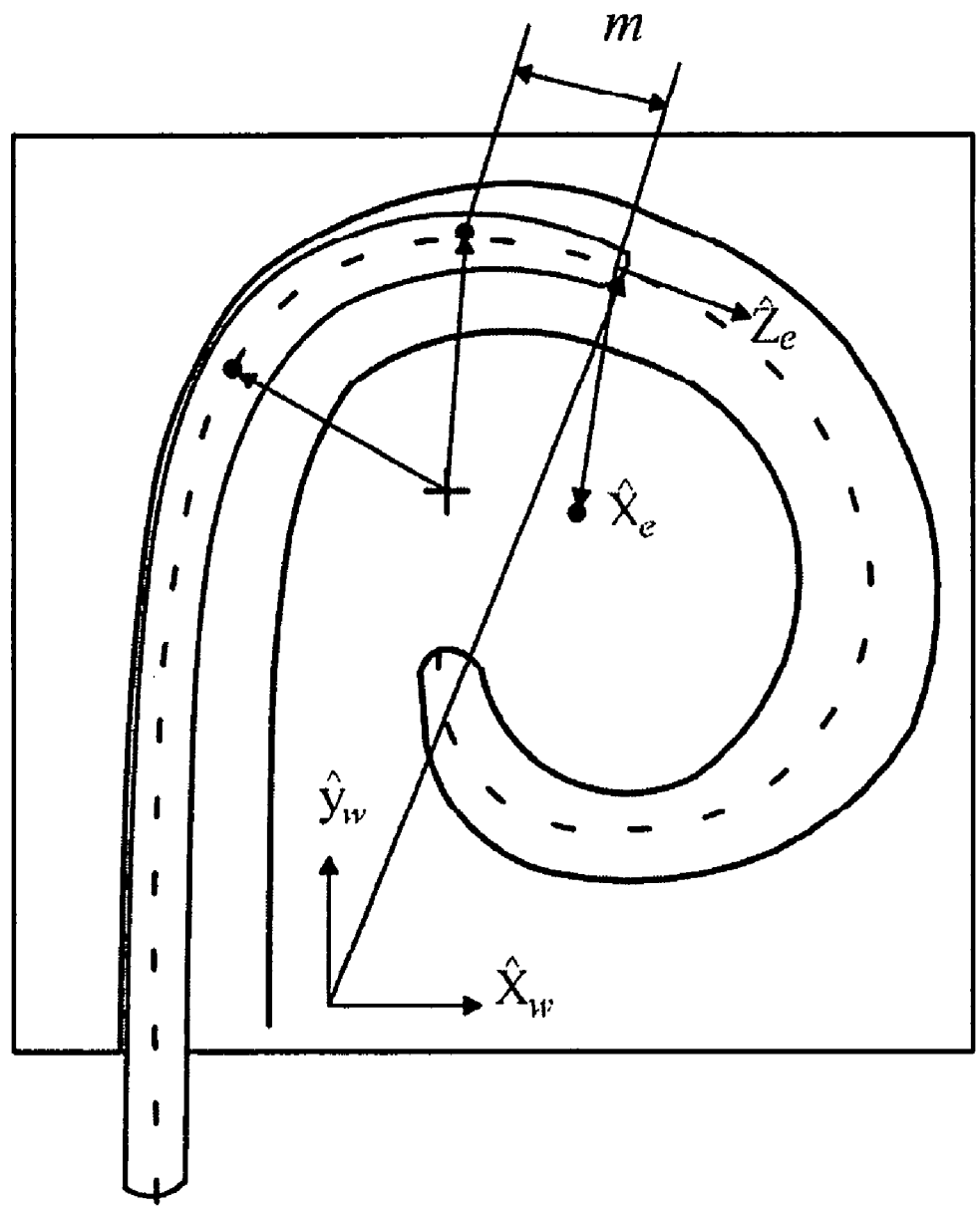
FIGS. 8 and 9 are images demonstrating some of the dimensions used to determine various mathematical relationships in accordance with some embodiments of the disclosed subject matter.
Figure 9:
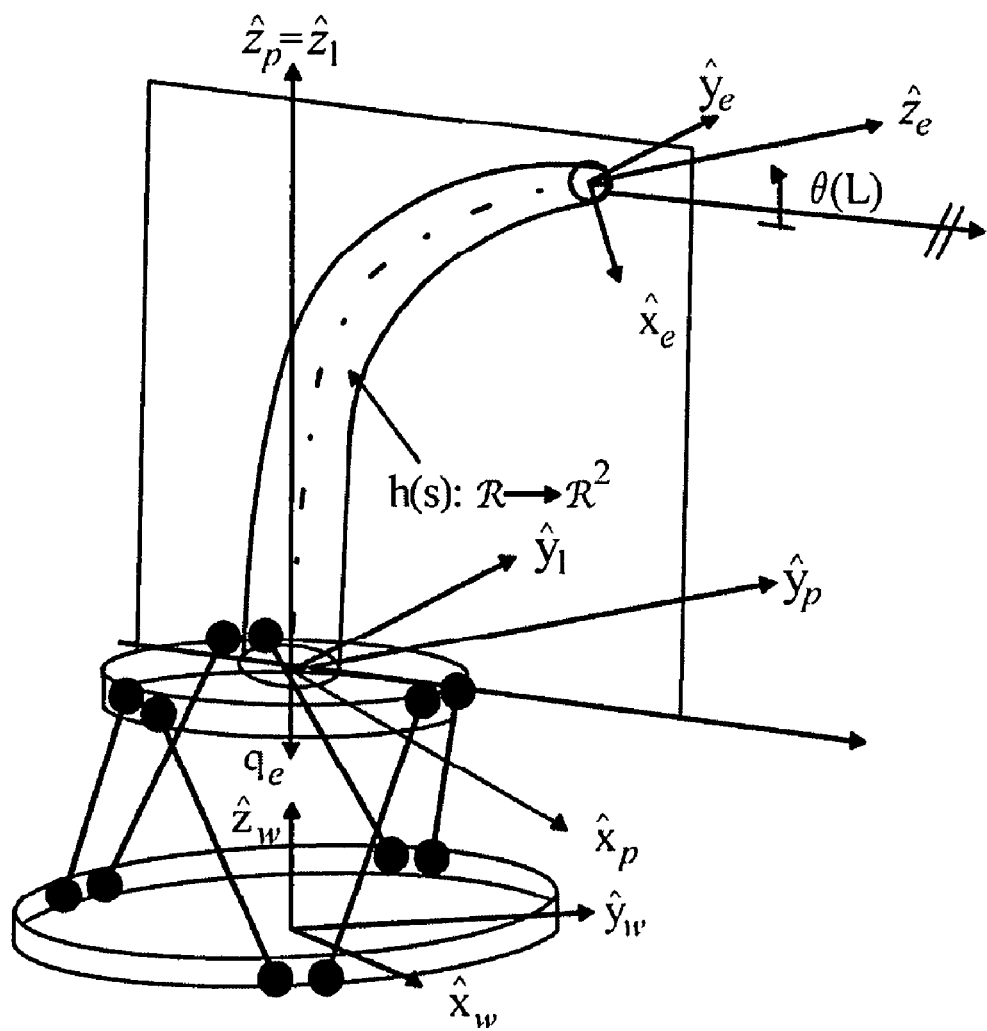

Referring to FIGS. 8 and 9, in some embodiments, an active-bending electrode array can be modeled kinematically. For example, let $\{\hat{x}_w, \hat{y}_w, \hat{z}_w\}$ refer to the world coordinate system, and $\{\hat{x}_l, \hat{y}_l, \hat{z}_l\}$ refer to the coordinate system characterizing the plane in which the active-bending electrode array deflects. Also, let $\{\hat{x}_p, \hat{y}_p, \hat{z}_p\}$ refer to a coordinate system attached to a moving stand where an insertion module is located. Coordinate system $\{\hat{x}_e, \hat{y}_e, \hat{z}_e\}$ is defined as being attached at the tip of an active-bending electrode array and aligned such that $\hat{x}_e$ lies in $\{\hat{x}_l, \hat{z}_l\}$ plane and $\hat{z}_e$ is the tangent to the active-bending electrode array at its tip. The shape of the active-bending electrode array can be characterized using the mathematical representation shown in equation 1, where $\theta$ refers to the angle of the curve tangent in the $\{\hat{x}_l, \hat{z}_l\}$ plane and s refers to the arc-length parameter along the curve h(s): $\mathfrak{R} \to \mathfrak{R}^2$ describing the backbone of the active-bending electrode array (i.e., the length from s=0 at the base of the active-bending electrode array to s=1 at the tip of the active-bending electrode array).

$$\theta(s) = \sum_{i=1}^{n} a_n \varphi_n(s) = a^t \varphi(s) \tag{1}$$

The active-bending electrode array can be assumed to bend in the plane $\{\hat{x}_l, \hat{z}_l\}$. The configuration of an active-bending electrode array can be controlled by $q_p$ and $q_e$, where $q_p$ designates the joint coordinates of an insertion module holding the active-bending electrode array and $q_e$ designates the joint variables of the electrode array. The electrode array coordinates, $q_e$, can be related to the bending angle at the tip of the active-bending electrode array according to $q_e = f(\theta(L))$. As shown in equation 2, each point along the backbone of an active-bending electrode array can be given by direct integration along h(s): $\mathfrak{R} \to \mathfrak{R}^2$ while accounting for any location contraction $\epsilon(s) < 0$ due to the actuation forces acting on the body of the active-bending electrode array (e.g., forces acting on the silicon rubber). $\epsilon(s)$ can be computed based on the stiffness properties of an active-bending electrode array and can, for example, be verified experimentally by visually tracking motions of markers along the active-bending electrode array's axis. Matrix $^wR_l$ can refer to the rotation matrix relating $\{\hat{x}_l, \hat{y}_l, \hat{z}_l\}$ coordinated system to $\{\hat{x}_w, \hat{y}_w, \hat{z}_w\}$ and $t(q_p)$ can refer to the position of a stand, where an insertion module is located, with respect to $\{\hat{x}_w, \hat{y}_w, \hat{z}_w\}$ Using the twist distribution $g(\theta_L, s)$, as in equation 3, one can define the instantaneous kinematics for each point along the backbone of the electrode array as in equation 4. The configuration vector (i.e., the position and orientation of each location coordinate system along the backbone) is defined by $x(s) \in \mathfrak{R}^{6 \times 1}$. $J_p$ refers to the instantaneous kinematics Jacobian of an insertion module such that $\dot{q}_p = \dot{J}_p \dot{x}_p$ where $\dot{x}_p$ is the linear and angular velocity of a movable stand. $J_e$ refers to the Jacobian of an active-bending electrode array to be derived. The first term of equation 4 represents the kinematics of the insertion module and the second term represents the kinematics of an active-bending electrode array.

$$r(s) = {}^wR_1 \int_0^s \left( (1 + \varepsilon(\tau)) \begin{bmatrix} \cos(a^t \varphi(\tau)) \\ 0 \\ \cos(a^t \varphi(\tau)) \end{bmatrix} \right) d\tau + t(q_p) \tag{2}$$

$$\dot{\theta}(s) = g(\theta_L, s) \dot{\theta}(L) \tag{3}$$

$$\dot{x}(s) = J_p^{-1} \dot{q}_p + {}^wR_1 J_e \dot{q}_e \tag{4}$$

Still referring to FIGS. 7 and 8, in some embodiments, a path-planning module can utilize a shape Jacobian to determine the required level of steering inside the cochlea. The shape Jacobian can define the relationship between the instantaneous velocity and the time derivative of an error vector describing the difference between the actual position of tele-robotic device and a time-varying curve that defines its desired shape. That is, the shape Jacobian can be used to determine the required level of steering inside the cochlea by comparing the actual position against the theoretical position and compensating for the difference. For example, the actual position of the insertion module can be calculated by using equation 5 wherein d represents the current depth of insertion into the body (e.g., insertion displacement), the active-bending electrode array is divided into m segments, and the configurations of m+1 points along the inserted portion by $p(\tilde{q})$, where $$\tilde{q} = [q_e^t, q_p^t]^t$$

refers to the augmented joint variables' vector. The theoretical location in the body can be determined using equation 6, wherein $p_d$ is a vector of m+1 configurations along the curve $c(s): \mathfrak{R} \to \mathfrak{R}^3$. Thus, for each insertion depth, d, an error vector can be quantified using equation 7. The distance between the center of the inner ear and the inserted portion of the electrode array is minimized using equation 8. The solution of equation 8 can be achieved using a mathematical optimization technique (e.g., least-squares sense) and will yield the value of the desired actuation variables $$\tilde{q} = [q_e^t, q_p^t]^t.$$

$$p(\tilde{q}) = \left[r(L), \left[r\left(L - \frac{j}{m}d\right)\right]^t\right]^t \quad j = 1, 2, 3 \ldots m \quad (5)$$

$$P_d = \left[c(L), \left[c\left(L - \frac{j}{m}d\right)\right]^t\right]^t \quad j = 1, 2, 3 \ldots m \quad (6)$$

$$e(d): p(q) - P_d \quad (7)$$

$$\text{Min}_{\tilde{q}}(e^t e) \quad (8)$$

Additionally or alternatively, a path planning module in accordance with some embodiments may calculate the path of an electrode array as follows. Let $s_q$ represent the electrode insertion depth and let $\theta_c(s)$ be the shape of the cochlea. Equation 9 returns the optimal value of q that minimizes the shape difference between the inserted portion of the electrode and the cochlea. The optimal value of q is found by calculating the objective function for all columns of $\Phi$ and the minimum is found by numerical interpolation between the columns that best approximate the minimum value of the objective function.

$$\underset{q}{\text{argmin}} \int_{L-s_q}^{L} (|\theta_C(s) - \theta(s)|^2) \quad (9)$$

In some embodiments, the distance between the electrode array and the wall of the cochlea can be calculated. The calculated distances between the electrode array and the wall of the cochlea can be used to lessen frictional forces between the electrode array and the cochlea. For example, equation 10 can be used to quantify the performance of an active-bending electrode array. $E(\theta)$ refers to the distance between the inserted portion of the electrode array and the wall of the cochlea and $\theta$ refers to the angle of the electrode curve tangent to the x-y plane. In some embodiments, equation 10 may be used to determine the optimal routing of an actuation thread.

$$\bar{E} = \int_{\theta_{min}}^{\theta_{max}} E(\theta) d\theta / (\theta_{max} - \theta_{min}) \quad (10)$$

The insertion force due to friction between the electrode and cochlea may be equivalent to friction force in a band brake system, which depends on the contact angle of the electrode with the external walls of the cochlea. To explain this, third-order polynomials can be fitted to the digitized data to represent the curve of the external wall of the electrode, $r_c$, and the curve of the outer wall of the cochlea, $r_l$. Using these polynomial representations a distance metric $e(\theta) = \|r_c(\theta) - r_l(\theta)\|_2$ $\theta \in [0, \phi]$ can be calculated (where $\phi$ is the insertion angle) and averaged for every insertion angle during the insertion as shown in equation (11).

$$\bar{e} = \varphi^{-1} \int_0^\varphi e(\theta) d\theta \quad (11)$$

This explains the decrease in the insertion forces when the electrode is actuated since the average distance metric is increased significantly compared to the passive electrode array. Moreover, the difference between the active electrode array and the passive electrode array becomes more prominent as the insertion depth increases.

In some embodiments, the speed of insertion is adjusted to minimize the force of insertion. For example, referring to equation 12, $f_s$ refers to the force and $m_s$ refers to force and moment measured by a force sensor. $\dot{X}_g$ refers to the twist (i.e., linear and angular velocity) of the parallel robot at the point where the electrode is supported. $\hat{z}_g$ refers to the tangent to the electrode at the point where the electrode is supported. Scalars that adjust the insertion speed along and perpendicular to the electrode tangent $\hat{z}_g$ are represented by $v_{ins}$ and $v_t$. The first term in equation 12 determines the insertion speed while the second term in equation 12 adjusts the velocity to follow the involute of the electrode shape as the insertion forces increase.

$$\dot{X}_g = v_{ins}\hat{z}_g + v_t((I - \hat{z}_g\hat{z}_g^t)f_s/\|(I - \hat{z}_g\hat{z}_g^t)f_s\|_2 \quad (12)$$

The insertion speed (i.e., $v_{ins}$) can be determined by equation 13. Where $v_{min}$ and $v_{max}$ are the minimal and maximal tolerable insertion speeds. The parameter t can be determined based on disparity between the measured insertion force intensity $f_{ins} = f_s^t \hat{z}_g$ and the magnitude of the typical insertion forces $\tilde{f}(\theta)$ for a non-steerable electrode based on a friction model or on experimental results. Equation 14 relies on the assumption that a steerable electrode will be able to follow the shape of the cochlea and to reduce insertion forces. Parameters $\alpha$ and $\beta$ can be determined experimentally. Parameter $\beta$ will have an inverse relationship with $v_{ins}$ (i.e., as $v_{ins}$ decreases as a result of large insertion forces, $\beta$ will be increased to provide more motion in the direction of the electrode involute).

$$v_{ins} = v_{min} + t\alpha(v_{max} - v_{min}), t \in [0,1], \alpha \in \mathfrak{R} \quad (13)$$

$$t = (\tilde{f}(\theta) - f_{ins})/\tilde{f}(\theta) \quad (14)$$

In some embodiments, the friction force between the walls of the inner ear (e.g., scala tympani) and the electrode array may be calculated and used to better the design of the electrode array. For example using equation 15 the deflection in an active-bending electrode array may be optimized to minimize frictional forces on an active-bending electrode array. f refers to the total friction force (i.e. insertion force) required. $f_{end}$ refers to any force action on the tip of the electrode array to prevent it from sliding against the walls of the cochlea. $f_{end}e^{u\theta}$ refers to the required force to overcome $f_{end}$ acting at the tip of the electrode array. $\theta$ refers to the total contact angle between the cochlea and the electrode array. $f_s e^{u\theta}$ refers to the expression for the coulomb friction due to contact pressure generated by the bending rigidity of the electrode array.

$$f = f_{end}e^{u\theta} + f_s e^{u\theta} \quad (15)$$

Other embodiments, extensions, and modifications of the ideas presented above are comprehended and are within the reach of one versed in the art upon reviewing the present disclosure. Accordingly, the scope of the present invention in its various aspects are not be limited by the examples presented above. The individual aspects of the present invention, and the entirety of the invention are to be regarded so as to allow for such design modifications and future developments within the scope of the present disclosure. For example, although specific features are described herein in certain combinations, the present invention may be practiced using any combination of any of all or a subset of these features. The present invention is limited only by the claims that follow.

What is claimed is:

1. A system for implanting a steerable array having an active-bending portion that includes an actuation thread into an inner ear of a patient, the system comprising:
   an insertion module including:
      a first end for holding a proximal end of the steerable array,
      a force sensor configured to detect force on the steerable array and to produce force information, and
      a position sensor configured to detect a position of the steerable array and to produce position information, the position information including an insertion depth;
   a bending actuator configured to implant the steerable array into the inner ear by applying tension to the actuation thread to bend the active-bending portion of the steerable array, wherein the steerable array is configured to be implanted in a manner in which the implanted steerable array is left within the inner ear when the implanting is complete;
   a controller in communication with the insertion module and bending actuator, the controller programmed to control the bending actuator to bend the active-bending portion of the steerable array based on: (a) a path plan determined from a model of the inner ear and (b) the position information including the insertion depth; and
   a first interface for communicating the force information and the position information to the controller, wherein the controller is in communication with the first interface and programmed to output the force information and the position information.

2. The system of claim 1, further comprising a force actuator configured to apply a determined force to the steerable array.

3. The system of claim 2, wherein the determined force is adapted to counteract an external force applied to the insertion module.

4. The system of claim 3, wherein the determined force is adapted to counter tremor in a hand holding the insertion module.

5. The system of claim 2, wherein the force actuator is configured to vibrates the steerable array.

6. The system of claim 1, wherein the path plan determined from the model of the inner ear is based on a three-dimensional extension of a two-dimensional template of the inner ear.

7. The system of claim 1, wherein the insertion module is mounted on a robotic device.

8. The system of claim 1, wherein the insertion module is a handheld device.

9. The system of claim 1, further comprising a monitor in communication with the controller that is configured to display the force information in relation to the position information.

10. The system of claim 1, further comprising a second interface in communication with the controller configured to receive input, from an input device, for moving the steerable array substantially in an insertion direction in the inner ear, the controller further programmed to control the insertion module based on the input from the input device.

11. The system of claim 10, wherein the controller is further programmed to control movement of the insertion module in directions other than the insertion direction that are adopted based on computations done by the controller.

12. The system of claim 1, wherein the controller is further programmed to control an orientation of insertion based on the path plan and the position information.

13. The system of claim 10, wherein the second interface is further configured to send a force feedback signal to the input device to provide force feedback to a user, the controller further programmed to send the force feedback signal to the second interface based at least in part on the force information.

14. The system of claim 1, wherein the controller is further programmed to control an insertion speed of the steerable array based on the force information.

15. The system of claim 10, wherein the controller is further programmed to control the insertion module to move the steerable array substantially in the insertion direction in the inner ear based on the force information.

16. The system of claim 10, wherein the controller is further programmed to control the insertion module based on the force information.

17. The system of claim 1, further comprising a memory in communication with the controller, wherein the memory is configured to store the path plan.

18. A system for implanting a steerable array into an inner ear of a patient, the system comprising:
   a steerable array having an active-bending portion, wherein the active-bending portion includes an actuation thread and is configured to bend when tension is applied to the actuation thread;
   an insertion module including:
      a first end for holding a proximal end of the steerable array,
      a force sensor configured to detect force on the steerable array and to produce force information, and
      a position sensor configured to detect a position of the steerable array and to produce position information, the position information including an insertion depth;
   a bending actuator configured to implant the steerable array into an inner ear by applying tension to the actuation thread to bend the active-bending portion of the steerable array, wherein the steerable array is configured to be implanted in manner in which the implanted steerable array is left within the inner ear when the implanting is complete;
   a controller in communication with the insertion module and bending actuator, the controller programmed to control the bending actuator to bend the active-bending portion of the steerable array based on: (a) a path plan determined from a model of the inner ear, and (b) the position information including the insertion depth; and
   a first interface for communicating the force information and the position information to the controller, wherein the controller is in communication with the first interface and programmed to output the force information and the position information.

19. The system of claim 18, further comprising a force actuator configured to apply a determined force to the steerable array.

20. The system of claim 19, wherein the force actuator is configured to vibrates the steerable array.

21. The system of claim 18, wherein the path plan determined from the model of the inner ear is based on a three-dimensional extension of a two-dimensional template of the inner ear.

22. The system of claim 18, further comprising a monitor in communication with the controller that displays the force information in relation to the position information.

23. The system of claim 18, further comprising a second interface in communication with the controller configured to receive input, from an input device, for moving the steerable array substantially in an insertion direction in the inner ear, the controller further programmed to control the insertion module based on the input from the input device.

* * * * *